US009186439B2

(12) United States Patent
Morishita et al.

(10) Patent No.: US 9,186,439 B2
(45) Date of Patent: Nov. 17, 2015

(54) DRUG-ELUTING CATHETER AND METHOD OF MANUFACTURING THE SAME

(75) Inventors: Ryuichi Morishita, Osaka (JP); Hironori Nakagami, Osaka (JP); Takashi Miyake, Osaka (JP); Makoto Mitamura, Osaka (JP); Hiroaki Nakajima, Tokyo (JP); Hiroaki Matsuda, Tokyo (JP); Nao Suizu, Miyazaki (JP); Yoshihumi Kawano, Miyazaki (JP); Kunihiko Takagi, Miyazaki (JP); Hiroyuki Tsujimoto, Osaka (JP); Yusuke Tsukada, Osaka (JP); Kaori Hara, Osaka (JP); Yohei Bando, Osaka (JP)

(73) Assignees: AnGes MG, Inc., Osaka (JP); Medikit Co., Ltd., Tokyo (JP); Hosokawa Micron Corporation, Osaka (JP)

( * ) Notice: Subject to any disclaimer, the term of this patent is extended or adjusted under 35 U.S.C. 154(b) by 404 days.

(21) Appl. No.: 12/921,443

(22) PCT Filed: Mar. 12, 2009

(86) PCT No.: PCT/JP2009/054720
§ 371 (c)(1),
(2), (4) Date: Sep. 8, 2010

(87) PCT Pub. No.: WO2009/113605
PCT Pub. Date: Sep. 17, 2009

(65) Prior Publication Data
US 2011/0022027 A1 Jan. 27, 2011

(30) Foreign Application Priority Data

Mar. 12, 2008 (JP) .................... 2008-063143
Sep. 29, 2008 (JP) .................... 2008-249611

(51) Int. Cl.
*A61L 29/16* (2006.01)
*A61M 25/10* (2013.01)
*B05D 5/00* (2006.01)
*A61L 29/08* (2006.01)
*A61M 25/00* (2006.01)

(52) U.S. Cl.
CPC ............ *A61L 29/085* (2013.01); *A61L 29/16* (2013.01); *A61M 25/0045* (2013.01); *A61M 25/10* (2013.01); *A61M 25/104* (2013.01); *A61M 25/1027* (2013.01); *A61L 2300/258* (2013.01); *A61L 2300/624* (2013.01); *A61L 2400/12* (2013.01); *A61M 2025/0057* (2013.01); *A61M 2025/105* (2013.01); *A61M 2025/1031* (2013.01); *A61M 2025/1075* (2013.01); *A61M 2025/1086* (2013.01)

(58) Field of Classification Search
None
See application file for complete search history.

(56) References Cited

U.S. PATENT DOCUMENTS

| 5,102,402 A * | 4/1992 | Dror et al. .................... 604/265 |
| 5,135,516 A | 8/1992 | Sahatjian et al. |
| 5,879,369 A | 3/1999 | Ishida |
| 6,369,039 B1 | 4/2002 | Palasis et al. |
| 7,008,411 B1 | 3/2006 | Mandrusov et al. |
| 7,758,892 B1 * | 7/2010 | Chen et al. .................... 424/497 |
| 7,851,209 B2 * | 12/2010 | Wei et al. .................... 435/288.7 |
| 7,897,751 B2 * | 3/2011 | Tsukada et al. ............. 536/24.5 |
| 7,972,648 B2 * | 7/2011 | Berckmans et al. .......... 427/2.1 |
| 8,529,929 B2 * | 9/2013 | Aoki et al. .................... 424/422 |
| 2002/0016574 A1 | 2/2002 | Wang et al. |
| 2004/0180828 A1 | 9/2004 | Shi |
| 2004/0249450 A1 | 12/2004 | Ishii |
| 2005/0261760 A1 | 11/2005 | Weber |
| 2006/0212106 A1 | 9/2006 | Weber et al. |
| 2010/0076544 A1 * | 3/2010 | Hoffmann et al. .......... 623/1.15 |
| 2010/0280452 A1 | 11/2010 | Chen et al. |

FOREIGN PATENT DOCUMENTS

| JP | 01-195863 | 8/1989 |
| JP | 09-500561 | 1/1997 |
| JP | 09-164191 | 6/1997 |
| JP | H11-089930 | 4/1999 |
| JP | 2003-521275 | 7/2003 |
| JP | 2004-357986 | 12/2004 |
| JP | 2006-518736 | 8/2006 |
| JP | 2007-099631 | 4/2007 |
| JP | 2007-119396 | 5/2007 |
| JP | 2007-215620 | 8/2007 |
| JP | 2007537827 A | 12/2007 |
| KR | 1020050063768 A | 6/2005 |
| KR | JP2007215620 A | 8/2007 |
| WO | WO 00/67816 | 11/2000 |

OTHER PUBLICATIONS

Hara, et al. (2006) "The effect of poly (aspartic acid-co-lactic acid) nanospheres on the lung metastasis of B16BL6 melanoma cells by intravenous administration", Oncology Reports, 16(6): 1215-20.*
Westcott, et al. (1998) "Formation and Adsorption of Clusters of Gold Nanoparticles on to Functional Silica Nanoparticle Surfaces", Lanmuir, 14: 5396-401.*
Dajee et al., "Blockade of Experimental Atopic Dermatitis via Topical NF-kB Decoy Oligonucleotide," Journal of Investigative Dermatology, 126(8):1792-1803 (2006).
Drug Delivery System 21(3):366 with partial English translation (2006).

(Continued)

Primary Examiner — Robert M Kelly
(74) Attorney, Agent, or Firm — Fish & Richardson P.C.

(57) ABSTRACT

Biocompatible nanoparticles 1 which entrap a bioactive substance and whose surface is positive-charge-modified are electrically adhered to a balloon portion 9 of a catheter main body 5 through a negatively charged resin layer 11, and thus a nanoparticle layer 12 is formed. After the catheter main body 5 is indwell in vivo, the nanoparticles 1 are gradually eluted from the nanoparticle layer 12 and are effectively delivered to cells.

25 Claims, 15 Drawing Sheets

(56) References Cited

OTHER PUBLICATIONS

Nakamura et al., "Molecular strategy using *cis*-element 'decoy' of E2F binding site inhibits neointimal formation in porcine balloon-injured coronary artery model," Gene Therapy, 9(8):488-494, (2002).

Takeuchi et al., "In Vivo Reduction of the Nuclear Factor-$_k$B Activity Using Synthetic ciz-Element Decoy Oligonucleotides Suppresses Initmal Hyperplasia in the Injured Carotid Arteries in Rabbits," Surgery Today, 37:575-583 (2007).

Tsukada et al., "NF$_k$ B Decoy Oligodeoxynucleotide . . . ," The 23rd Symposium on Particulate Preparations and Designs, 23:122-125 (with partial English translation) (2006).

Egashira et al., "NF-$_k$B Decoy ni yoru . . . ," The 38th Japan Atherosclerosis Society, vol. 38, p. 148 (with partial English translation) (2006).

Tomita et al., "Transcription Factors as Molecular Targets: Molecular Mechanisms of Decoy ODN and their Design," Current Drug Targets (4): 603-608 (2003).

Tsujimoto et al., "NF$_k$B Decoy Oligodeoxynucleotide . . . ," Society of Powder Technology, 42:32-37 (with partial English translation) (2007).

Vos et al., "NF$_k$B decoy oligodeoxynucleotides reduce monocyte infiltration in renal allografts," FASEB Journal, 14(5):815-822 (2000).

Yamasaki et al., "Inhibition of NF$_k$B activation using cis-element 'decoy' of NFkB binding site reduces neointimal formation in porcine balloon-injured coronary artery model," Gene Therapy, 10(4): 356-364 (2003).

Yokoseki et al., "*cis* Element Decoy Against Nuclear Factor—kB Attenuates Development of Experimental Autoimmune Myocarditis in Rats," Circulation Research, pp. 899-906 (2001).

Yoshimura et al., "Inhibition of intimal hyperplasia after balloon injury in rat carotid artery model using cis-element 'decoy' of nuclear factor-$_k$B binding site as a novel molecular strategy," Gene Therapy, .8(21):1635-1642, (2001).

Relevant portion of Chapter 12 "Layer-by-layer electrostatic self-assembly building nanostructured materials" from book entitled "Materials Sciences and Engineer" and its English translations; (5 pages), published in Jul. 2007.

Dajee et al., *Blockade of Experimental Atopic Dermatitis via Topical NF-κB Decoy Oligonucleotide*, Journal of Investigative Dermatology, 126:1792-1803 (2006).

\* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: NFkappaB Decoy

<400> SEQUENCE: 1
ccttgaaggg atttccctcc                                              20

<210> SEQ ID NO 2
<211> LENGTH: 22
<212> TYPE: DNA
<213> ORGANISM: Artificial Sequence
<220> FEATURE:
<223> OTHER INFORMATION: NFkappaB Decoy

<400> SEQUENCE: 2
agttgagggg actttcccag gc                                           22
```

```
<210> SEQ ID NO 3
<211> LENGTH: 19
<212> TYPE: DNA
<213> ORGANISM: Artificial Sequence
<220> FEATURE:
<223> OTHER INFORMATION: NFkappaB Decoy

<400> SEQUENCE: 3
agttgaggac tttccaggc                                              19
```

DRUG-ELUTING CATHETER AND METHOD OF MANUFACTURING THE SAME

CROSS-REFERENCE TO RELATED APPLICATIONS

This application is a National Stage application under 35 U.S.C. §371 of International Application No. PCT/JP2009/054720, having an International Filing Date of Mar. 12, 2009, which claims priority to Japanese Patent Application Serial No. JP 2008-249611, filed Sep. 29, 2008 and Japanese Patent Application Serial No. JP 2008-063143, filed Mar. 12, 2008. The disclosures of the prior applications are considered part of (and are incorporated by reference in) the disclosure of this application.

TECHNICAL FIELD

The present invention relates to a dilation catheter that is inserted into a lumen in vivo such as a blood vessel and keeps a stenosis or obstruction open, and more particularly relates to a drug-eluting catheter coated with biocompatible nanoparticles entrapping a bioactive substance and a method of manufacturing the drug-eluting catheter.

BACKGROUND ART

In recent years, as lifestyles have been westernized and the population has been aging, more and more people have suffered from atherosclerotic diseases such as myocardial infarction, angina pectoris, cerebral apoplexy and peripheral vascular diseases even in our country. As a reliable treatment for such atherosclerotic diseases, percutaneous transluminal angioplasty (hereinafter referred to as "PTA"), such as percutaneous transluminal coronary angioplasty for a coronary artery of a heart, which surgically dilates a stenosis or obstruction of a blood vessel, is widely used.

PTA is a manipulative technique in which a thin tube (balloon catheter) with a balloon at its end is passed through a stenosis within a blood vessel, then the balloon at the end is inflated to dilate the stenosed blood vessel, and thus normal blood flow is restored. By doing this, the lumen of the blood vessel in an affected area is dilated, and thus the blood flow through the lumen of the blood vessel is increased. In addition to atherosclerotic diseases, PTA is also used such as in a stenosis treatment for a shunt blood vessel formed in an arm of a hemodialysis patient.

In general, the portion of a blood vessel that has been subjected to PTA is damaged such as by the detachment of endothelial cells and the injury of elastic laminas, and a vascular intima grows as a healing reaction for a vascular wall, with the result that restenosis occurs in about 30 to 40% of the stenosed areas that have been successfully dilated by PTA.

More specifically, human restenosis is considered to result primarily from an inflammatory process that occurs one to three days after PTA due to the adhesion and invasion of monocytes and the intimal thickening formation process of smooth muscle cells which grow most rapidly about forty five days after PTA. Since, when restenosis occurs, it is necessary to perform PTA again, the establishment of prophylaxis and treatment thereof is urgently required.

To meet the requirement, attempts have been widely proposed to reduce the restenosis rate by using a drug-eluting device in which an anti-inflammatory drug or a smooth muscle cell growth inhibitor is carried on the surface of a stent or balloon catheter made of a metal or high-polymer material and thereby releasing the drug locally in a site of a lumen where the device is indwelt over a long period of time. For example, in patent documents 1 and 2, there are proposed drug-eluting catheters in which the expanding portion (balloon) of the catheter is polymer coated, and a therapeutic drug such as a nucleic acid drug is incorporated into the polymer coating.

Since restenosis results primarily from smooth muscle cell growth, it is determined that it is most effective to inhibit the growth of the smooth muscle cells during a time period from the date when the growth of the smooth muscle cells is found in an intimal as a pathological finding, that is, the date when 30 days elapse after the start of a treatment to the date when the cells grow most rapidly, that is, the date when 45 days elapse. Hence, it is considered that it is most effective to design a drug-eluting catheter such that the amount of drug released peaks at least both during a period of 10 days after the start in order to inhibit an inflammatory process and during a period of 30 to 60 days in order to inhibit the growth of the smooth muscle cells and that the drug necessary to indicate its efficacy is evenly released for each period.

However, since, in the methods of patent documents 1 and 2, the polymer layer is decomposed in vivo and then the drug is released, the drug is released insufficiently in the early stage of the indwelling of the catheter, and thus it is impossible to effectively inhibit an inflammatory process occurring during a period of 1 to 3 days after the catheter is indwelt. When a hydrogel polymer is used as in patent document 1, since a water-soluble drug such as a decoy oligonucleotide is eluted in a short period of time, it is not easy to control the rate at which the drug is released.

In patent document 3, there is disclosed a drug-eluting stent (hereinafter referred to as a "DES") in which a first bioactive substance is contained in a polymer layer formed on the surface of the stent, and a biocompatible nano- or microcapsule entrapping a second bioactive substance is further contained, and thus it is possible to release the first bioactive substance in the early stage and then gradually release the second bioactive substance within the capsule. According to the method of patent document 3, a suspension of nanoparticles is sprayed or applied onto the main body of the stent or the main body of the stent is immersed in the suspension of nanoparticles, and thus the nanoparticles are adhered to the stent main body. However, with this type of method, it is difficult to uniformaly adhere a sufficient number of nanoparticles.

Here, the structure of a conventional biocompatible nanoparticle is shown in FIG. 19. The surface of the conventional biocompatible nanoparticle (hereinafter simply referred to as the "nanoparticle") 1 is coated with polyvinyl alcohol 2; a bioactive substance 3 is entrapped therewithin; and, in general, the surface is negatively charged. However, since a cell membrane in vivo is negatively charged, an electrical repulsion force disadvantageously causes the nanoparticle as shown in FIG. 19 to be poorly adhered to cells. In order for the entrapped bioactive substance to be locally and effectively incorporated into a lesion such as a stenosis, it is necessary to further enhance the movement of the nanoparticles into the cells.

Moreover, since biocompatible polymers are generally hydrophobic (liposoluble) and thus liposoluble bioactive substances alone can be entrapped into nanoparticles with high probability, it is difficult to sufficiently coat, by the method of patent document 3, the surface of the stent with a hydrophilic (water-soluble) bioactive substance such as a nucleic acid or a gene.

To overcome this problem, in patent document 4, there is disclosed a DES in which biocompatible nanoparticles whose surface is positive-charge-modified are electrically adhered to the main body of the stent, and there is also disclosed a method of manufacturing a DES by adhering the nanoparticles to the stent main body in an electrical continuous state, using electrophoresis, ultrasonic mist or the like. In patent document 5, there is disclosed a medical device having nanocapsules (nanoparticles) composed of a therapeutic drug, a magnetic or paramagnetic material and a polyelectrolyte multilayer shell, and a catheter is described therein as an example of the medical device.

Patent document 1: JP-T-H09-500561
Patent document 2: JP-T-2003-521275
Patent document 3: JP-A-2004-357986
Patent document 4: JP-A-2007-215620
Patent document 5: JP-T-2006-518736

DISCLOSURE OF THE INVENTION

Problems to be Solved by the Invention

However, since, in the method of patent document 4, the stent main body needs to be formed of a conductive material such as a metal, it is difficult to apply the method to a balloon catheter whose expandable portion (balloon portion) is formed of a low conductive resin. Patent document 5 only discloses that, in order to simply control the release of the entrapped drug, the nanoparticles are formed with the degradable polyelectrolyte, and does not disclose at all an example of a drug-eluting catheter coated with biocompatible nanoparticles whose surface is positive-charge-modified, that is, what configuration the actually manufactured nanoparticles have and to what degree the nanoparticles are adhered to cells or to what degree they are incorporated into the cells.

In view of the problem described above, the present invention has an object to provide a drug-eluting catheter that can effectively deliver a bioactive substance into cells by being coated with biocompatible nanoparticles which entrap a liposoluble or water-soluble bioactive substance with high probability and which satisfactorily move into cells, that has excellent handleability and that is expandable. The invention has another object to provide a simple and inexpensive method of manufacturing the drug-eluting catheter.

Means for Solving the Problem

To achieve the above object, according to the present invention, there is provided an expandable drug-eluting catheter in which the surface of a negative-charge-modified expandable portion is coated with a biocompatible nanoparticle which entraps a bioactive substance and whose surface is positive-charge-modified.

With this configuration, it is possible to adhere nanoparticles whose surface is positively charged even to a resin expandable portion. Since the nanoparticles with which the expandable portion is coated are positively charged, it is possible to provide a drug-eluting catheter in which the adherence of the nanoparticles to negatively charged cell membranes is increased and the bioactive substance internally entrapped reach cells more effectively. For example, when a polymer material of which the biocompatible nanoparticles are formed is liposoluble, a liposoluble bioactive substance is entrapped more effectively. In addition, since the surface of the nanoparticles is positively charged, it is possible to entrap a water-soluble and anionic bioactive substance more effectively, and select from a larger number of bioactive substances the bioactive substance with which the expandable portion can be coated.

In the drug-eluting catheter of the present invention configured as described above, the expandable portion is negative-charge-modified by a polycarboxylic acid or a polycarboxylic acid derivative.

With this configuration, it is possible to easily and negatively charge the surface of the expandable portion.

In the drug-eluting catheter of the present invention configured as described above, the polycarboxylic acid is one or more selected from the group consisting of polymers of acrylic acid, methacrylic acid, maleic acid, fumaric acid, aspartic acid and glutamic acid; a carboxymethyl derivative of starch, cellulose or polyvinyl alcohol; alginic acid; and pectin.

With this configuration, it is possible to provide a drug-eluting catheter that only slightly affects humans and is highly safe.

In the drug-eluting catheter of the present invention configured as described above, the polycarboxylic acid derivative is an acid anhydride derivative or ester derivative of a polymer of acrylic acid, methacrylic acid or maleic acid.

With this configuration, it is possible to perform negative-charge-modification that strongly adheres nanoparticles whose surface is positively charged and that is less irritating and toxic.

In the drug-eluting catheter of the present invention configured as described above, the polycarboxylic acid derivative is a maleic anhydride copolymer.

With this configuration, it is possible not only to provide a highly safe drug-eluting catheter but also to more easily handle the drug-eluting catheter when the negative-charge-modification is performed.

In the drug-eluting catheter of the present invention configured as described above, the maleic anhydride copolymer is one or more selected from the group consisting of a maleic anhydride-methyl vinyl ether copolymer, a maleic anhydride-styrene copolymer and a maleic anhydride-ethylene copolymer.

With this configuration, it is possible to easily and inexpensively manufacture a highly safe drug-eluting catheter using a maleic anhydride copolymer that is easily available in particular and is easy to handle.

In the drug-eluting catheter of the present invention configured as described above, the biocompatible nanoparticle is positive-charge-modified by adhering a cationic polymer to the surface.

With this configuration, it is possible to easily and positively charge the surface of the nanoparticles.

In the drug-eluting catheter of the present invention configured as described above, the cationic polymer is a chitosan.

With this configuration, it is possible to provide a highly safe drug-eluting catheter that does not affect humans.

In the drug-eluting catheter of the present invention configured as described above, the biocompatible nanoparticle is formed of any of polylactic acid, polyglycolic acid, a lactic acid-glycolic acid copolymer and a lactic acid-aspartic acid copolymer.

With this configuration, it is possible to provide a drug-eluting catheter that is less irritating and toxic and that can gradually release the bioactive substance by the decomposition of the biocompatible polymer.

In the drug-eluting catheter of the present invention configured as described above, the bioactive substance is a nucleic acid compound.

With this configuration, it is possible to safely and effectively introduce a nucleic acid compound into an affected area to perform a nucleic-acid-based treatment; for example, it is possible to easily manufacture the drug-eluting catheter that is unlikely to cause restenosis, for example, when the catheter is applied to a stenosis of a blood vessel.

In the drug-eluting catheter of the present invention configured as described above, the nucleic acid compound is one or more selected from the group consisting of a plasmid DNA, a gene, a decoy, an siRNA, an oligonucleotide, an antisense oligonucleotide, a ribozyme and an aptamer.

With this configuration, it is possible to provide a drug-eluting catheter that is particularly suitable as a nucleic compound therapy tool.

In the drug-eluting catheter of the present invention configured as described above, the nucleic acid compound is an NFκB decoy oligonucleotide.

With this configuration, it is possible to provide a drug-eluting catheter that inhibits the generation of a cytokine or the like which binds to an NFκB to cause an inflammation, that reduces an acute phase inflammatory response when PTA is performed, and that thereby effectively can prevent restenosis In the present invention, the drug-eluting catheter configured as described above is used as an intravascular catheter.

With this configuration, it is possible to produce the beneficial effect of preventing resenosis in the area of a blood vessel that has been subjected to PTA.

In the present invention, the drug-eluting catheter configured as described above is a balloon catheter having a balloon as the expandable portion.

With this configuration, it is possible to easily dilate a stenosis by inserting the catheter into the stenosis within a blood vessel and then expanding the balloon.

In the drug-eluting catheter of the present invention configured as described above, a recess is formed in the surface of the balloon.

With this configuration, it is possible to carry a large number of biocompatible nanoparticles in the recesses, push the nanoparticles out of the recesses by eliminating the recesses as the balloon is expanded, and effectively adhere them to the vascular wall of the stenosis.

In the drug-eluting catheter of the present invention configured as described above, the recess is circular or elliptical.

With this configuration, it is possible to easily deform or eliminate the recesses by expanding the balloon.

According to the present invention, there is provided a method of treating vascular stenosis or dialysis shunt stenosis, using the drug-eluting catheter configured as described above.

With this configuration, it is possible to effectively treat resenosis in the area of a blood vessel that has been subjected to PTA and stenosis in a shunt blood vessel formed in an arm of a hemodialysis patient.

According to the present invention, there is provided a method of manufacturing a drug-eluting catheter that includes: a nanoparticle formation step of adding a mixed solution of at least a solution of a bioactive substance and a solution obtained by dissolving a biocompatible polymer in an organic solvent to an aqueous solution obtained by dissolving at least a cationic polymer, entrapping the bioactive substance into the biocompatible polymer and generating a suspension of a biocompatible nanoparticle whose surface is positive-charge-modified; a negative-charge-modification step of negative-charge-modifying an expandable portion of a catheter main body; a nanoparticle adherence step of forming a nanoparticle layer by adhering the biocompatible nanoparticle to the negative-charge-modified expandable portion; and a drying step of drying the nanoparticle layer.

With this method, since a uniform nanoparticle layer is strongly formed on the expandable portion, it is possible to easily and inexpensively manufacture an expandable drug-eluting catheter that can effectively deliver the bioactive substance into cells and that is easy to handle.

According to the present invention, in the method of manufacturing the drug-eluting catheter configured as described above, the negative-charge-modification step is performed by dipping the expandable portion in the solution of a polycarboxylic acid or a polycarboxylic acid derivative.

With this method, it is possible to easily and effectively form a negatively charged uniform resin layer.

According to the present invention, in the method of manufacturing the drug-eluting catheter configured as described above, an anionic bioactive substance is further added to the suspension of the biocompatible nanoparticle.

With this method, it is possible to manufacture a drug-eluting catheter in which, since the nanoparticles are attracted and adhered to the negative-charge-modified expandable portion with an anionic bioactive substance electrostatically carried by positive charges on the surface of the nanoparticles, the anionic bioactive substance, such as a nucleic acid or a gene, that is difficult to perform coating with is adhered to the expandable portion at a high concentration.

According to the present invention, in the method of manufacturing the drug-eluting catheter configured as described above, the nanoparticle adherence step is repeated a plurality of times to further place a nanoparticle layer on the nanoparticle layer formed on the expandable portion.

With this method, it is possible to increase the number of nanoparticles with which the coating is performed and make uniform the entire nanoparticle layer on the expandable portion.

According to the present invention, in the method of manufacturing the drug-eluting catheter configured as described above, the nanoparticle adherence step is repeated a plurality of times to form the nanoparticle layers of biocompatible nanoparticles entrapping different bioactive substances one on top of another or in a mosaic pattern.

With this method, it is possible to manufacture a drug-eluting catheter in which, when nanoparticles entrapping a bioactive substance that is eluted in a short period of time after the catheter is indwelt in vivo are adhered to an external layer, and nanoparticles entrapping a bioactive substance that is eluted after a long period of time elapses are adhered to an internal layer, it is possible to control, in a planned manner, periods during which two or more types of bioactive substances are eluted.

According to the present invention, in the method of manufacturing the drug-eluting catheter configured as described above, an impregnation step of impregnating the nanoparticle layer with the solution of a biodegradable polymer is included.

With this method, it is possible to control a speed at which the nanoparticles are eluted from the expandable portion and prevent the nanoparticles from aggregating to become an insoluble film.

According to the present invention, in the method of manufacturing the drug-eluting catheter configured as described above, in the impregnation step, the bioactive substance is further added to the solution of the biodegradable polymer.

With this method, it is possible to make the bioactive substance entrapped into the biodegradable polymer outside the nanoparticles act rapidly and make the bioactive substance entrapped into the nanoparticles act slowly and continuously.

According to the present invention, in the method of manufacturing the drug-eluting catheter configured as described above, the biodegradable polymer with which the nanoparticle layer is impregnated in the impregnation step degrades in vivo more rapidly than the biocompatible polymer forming the biocompatible nanoparticle.

With this method, since the nanoparticles are diluted from the expandable portion by the degradation of the biodegradable polymer and are moved into cells, and then the bioactive substance is gradually released by the degradation of the biocompatible polymer forming the nanoparticles, it is possible to manufacture a drug-eluting catheter that more efficiently introduces the bioactive substance into the cells and that easily controls the introduction of the bioactive substance.

BEST MODE FOR CARRYING OUT THE INVENTION

Figure 1:
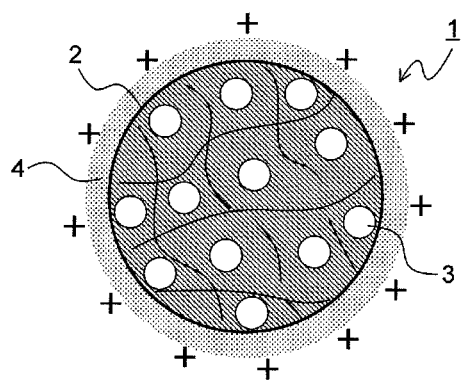
FIG. 1 A schematic diagram showing the structure of a nanoparticle which is used in a drug-eluting catheter of the present invention and in which the surface of the particle is positive-charge-modified and a bioactive substance is entrapped into the particle.

Embodiments of the present invention will be described in detail below with reference to the accompanying drawings. A method of manufacturing a drug-eluting catheter of the invention includes: a step of forming biocompatible nanoparticles which entrap a liposoluble or water-soluble bioactive substance and whose surface is positively charged (positive-charge-modified); a negative-charge-modification step of negatively charging (negative-charge-modifying) the expandable portion of the main body of the catheter; a nanoparticle adherence step of forming a nanoparticle layer by adhering the nanoparticles to the negative-charge-modified expandable portion; and a drying step of drying the nanoparticle layer.

In general, most particles dispersed in a liquid are positively or negatively charged; a layer (fixed layer) formed by strongly attracting and fixing ions of the opposite charge to the surface of the particles and a layer (diffusion layer) outside the fixed layer constitute a so-called diffuse electric double layer. It is estimated that part of the inner side of the diffusion layer and the fixed layer move together with the particles.

A zeta potential is a potential of a plane (sliding plane) where the above movement occurs, with respect to the potential of an electrically neutral region sufficiently away from the particles. As the absolute value of the zeta potential increases, the repulsion force between the particles becomes greater, and thus the stability of the particles is increased, whereas, as the zeta potential approaches zero, the particles are more likely to aggregate. Thus, the zeta potential is used as an index for the diffused state of particles.

Hence, in order to increase the adhesiveness to negatively charged cell membranes and effectively move the nanoparticles into cells, it is preferable to charge the surface of the nanoparticles such that it has a positive zeta potential. In the present invention, a cationic polymer is added to a poor solvent in a nanoparticle formation step (described later). In this way, the surface of the formed nanoparticle is modified (coated) with the cationic polymer, and thus the zeta potential of the surface of the particles becomes positive.

By positively charging the surface of the nanoparticle, it is possible to actively adhere the nanoparticles to the negative-charge-modified expandable portion of the catheter main body. This allows the nanoparticles to be adhered more effectively, and the nanoparticles once adhered are strongly fixed to the expandable portion, with the result that the nanoparticles can be prevented from being detached during the production process and at the time of insertion into a living body and of expansion. The process from a step of entrapping the bioactive substance into the nanoparticles to a step of adhering them to the expandable portion will be described step by step below.

(Nanoparticle Formation Step)

The biocompatible nanoparticles used in the present invention are manufactured by entrapping the bioactive substance into the nanoparticles using a spherical crystallization technique with which the bioactive substance and a biocompatible polymer can be processed into nanosized particles (nanospheres) having an average diameter of less than 1000 nm. Since the spherical crystallization technique is a particle preparation technique that is performed without producing a high shearing force, it can also be suitably used especially for a bioactive substance, such as a nucleic acid compound, susceptible to an external stress.

With the spherical crystallization technique, it is possible to design spherical crystal particles by controlling the generation and growth process of crystals in the final process of compound synthesis and to process them by directly controlling their physical properties. As one of the spherical crystallization techniques, there is an emulsion solvent diffusion method (ESD method).

The ESD method is a technology for manufacturing nanoparticles on the following principle. In this method, there are used two types of solvents, namely, a good solvent that can dissolve a PLGA (lactic acid/glycolic acid copolymer) and the like serving as a base polymer entrapping the bioactive substance and a poor solvent that does not dissolve the PLGA by contrast. As this good solvent, an organic solvent such as acetone is used that dissolves the PLGA and mixes with the poor solvent. As the poor solvent, a polyvinyl alcohol aqueous solution or the like is generally used.

In the operation procedure, the PLGA is first dissolved in the good solvent, and then a bioactive substance solution is added to and mixed with the good solvent so that the PLGA is not precipitated. This mixed solution of the PLGA and the bioactive substance is dropped into the poor solvent while stirred, and then the good solvent (organic solvent) in the mixed solution is rapidly diffused and moved into the poor solvent. Consequently, the good solvent is self-emulsified in the poor solvent, and submicron-sized emulsion drops of the good solvent are generated. Moreover, since the interdiffusion of the good solvent and the poor solvent causes the organic solvent to continuously diffuse from the emulsion to the poor solvent, the PLGA and the bioactive substance within the emulsion drops are decreased in solubility, with the result that PLGA nanoparticles which are spherical crystal particles entrapping the bioactive substance are finally generated.

With the spherical crystallization technique described above, since the nanoparticles are formed by a physicochemical technique and the resulting nanoparticles are substantially spherical, it is possible to easily form homogeneous nanoparticles without consideration of residues of a catalyst and a raw compound. Furthermore, in the present invention, the cationic polymer is added to the poor solvent, and thus the surface of the nanoparticles is coated with the cationic polymer, with the result that the surface of the particles is positively charged. The structure of such a nanoparticle is shown in FIG. 1. The surface of the nanoparticle 1 is coated with polyvinyl alcohol 2, and the bioactive substance 3 is entrapped into the nanoparticle 1. Moreover, the outer surface of the polyvinyl alcohol 2 is coated with the cationic polymer 4, and the cationic polymer 4 makes the outer surface have a positive zeta potential.

Figure 19:
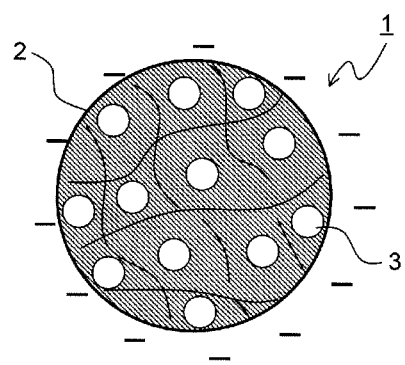
FIG. 19 A schematic diagram showing the structure of conventional nanoparticles.

Since cell membranes in vivo are negatively charged but the surface of the nanoparticles manufactured by the conventional spherical crystallization technique generally has a negative zeta potential (see FIG. 19), an electrical repulsion force disadvantageously causes the nanoparticles to be poorly adhered to cells. Hence, it is also preferable to charge, as in the present invention, the surface of the nanoparticles with the cationic polymer such that it has a positive zeta potential, because this increases the adhesiveness to the negatively charged cell membranes and enhances the movement of the bioactive substance into the cells.

Examples of the cationic polymer include: chitosans and chitosan derivatives; cationic cellulose obtained by bonding a plurality of cationic groups to cellulose; polyamino compounds such as polyethylenimine, polyvinylamine and polyallylamine; polyamino acids such as polyomithine and polylysine; polyvinylimidazole; polyvinylpyridinium chloride;

alkylaminomethacrylate quaternary salt polymers (DAM); and alkylaminomethacrylate quaternary salt/acrylamide copolymers (DAA). In particular, a chitosan or its derivative is preferably used.

Chitosans are cationic natural polymers which are contained in the shells of shrimps, crabs and insects, and in which a large number of molecules of glucosamine, one type of sugar having an amino group, are bonded. Chitosans have characteristics such as emulsion stability, shape retention, biodegradability, biocompatibility and antibacterial activity, and is therefore widely used as raw materials for cosmetics, food, clothing, drugs and the like. By adding a chitosan to the poor solvent, it is possible to manufacture the nanoparticles that do not affect humans and are highly safe.

When a highly cationic polymer among cationic polymers is used, the zeta potential becomes a greater positive value, and thus electrical adsorbability in the nanoparticle adherence step, which will be described later, is increased, and the resulting higher repulsion force between the particles increases the stability of the particles in the suspension. For example, a chitosan derivative (cationic chitosan), such as N-[2-hydroxy-3-(trimethylammonio)propyl]chitosan chloride, in which part of the originally-cationic chitosan is quaternized to further increase the cationic properties, is preferably used.

When the bioactive substance entrapped into the nanoparticles is anionic (exists as a negatively charged anionic molecule in the aqueous solution), the addition of a cationic polymer to the negative solvent can increase the rate at which the bioactive substance is entrapped into the nanoparticles. In general, when the bioactive substance entrapped is hydrophilic (water-soluble), the bioactive substance dispersed and mixed in the good solvent leaks and dissolves in the poor solvent, and only the polymer of the nanoparticles is precipitated, with the result that almost no bioactive substance is entrapped. However, when the cationic polymer is added to the poor solvent, it is believed that the interaction of the cationic polymer adsorbed on the surface of the nanoparticles with the anionic bioactive substance present on the surface of the emulsion drops can prevent the bioactive substance from leaking in the poor solvent.

In order to enhance the affinity and the dispersion stability of the anionic bioactive substance in the good solvent, it is alternatively possible to add to the good solvent a cationic lipid such as DOTAP (N-[1-(2,3-Dioleoyloxy)propyl]-N,N,N-trimethylammonium salts) and thereby form a composite with the anionic bioactive substance. Since the cationic lipid released in the cell may cause cytotoxicity, caution should be taken in the amount of the cationic lipid added.

Figure 2:
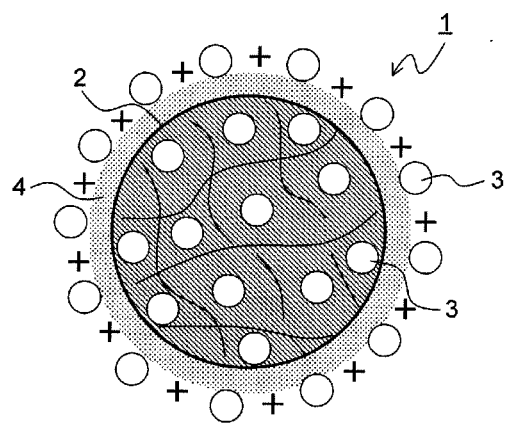
FIG. 2 A schematic diagram showing the structure of a nanoparticle which is used in the drug-eluting catheter of the present invention and in which the surface of the particle is positive-charge-modified and the bioactive substance is entrapped into the particle and is also carried on the surface of the particle.

Furthermore, when the bioactive substance is anionic, the addition of the bioactive substance at the time of making the nanoparticles composite by freeze-drying allows a predetermined amount of the bioactive substance present as negatively charged anionic molecules in the aqueous solution to be carried on the surface of the nanoparticles through electrostatic interaction. The structure of such a nanoparticle is shown in FIG. 2. The surface of the biocompatible nanoparticle 1 is coated with the polyvinyl alcohol 2. Its outer surface is coated with the cationic polymer 4, and the cationic polymer 4 makes the outer surface have a positive zeta potential. The bioactive substance 3 is entrapped into the nanoparticle 1, and is also electrostatistically carried on the surface of the nanoparticle 1.

Hence, with respect to the anionic bioactive substance that is significantly difficult to entrap into the liposoluble (hydrophobic) nanoparticles, its total content including the content both within and on the surface of the nanoparticles can also be increased. Aside from the bioactive substance that dissolves from the surface of the nanoparticle immediately after the administration, the bioactive substance that is gradually released out of the nanoparticles is made act, and this enables the medicinal preparation to produce both an instantaneous effect and a continuous effect.

When a removal step is provided of removing an extra amount of polyvinyl alcohol such as by centrifugation before the freeze-drying, part of the cationic polymer on the surface of the particles may be removed along with the polyvinyl alcohol. Hence, it is preferable to provide a step of immersing the nanoparticles in the cationic polymer solution again after the removal step.

The types of good solvent and poor solvent used in the spherical crystallization technique are determined according to the types of bioactive substances entrapped into the nanoparticles or the like; they are not particularly limited. However, since the biocompatible nanoparticles are used as a material for a drug-eluting catheter that is inserted into a living body, they need to be highly safe to humans and only slightly affect the environment.

Examples of the poor solvent include water and water containing a surface-active agent. For example, a polyvinyl alcohol aqueous solution containing polyvinyl alcohol as a surface-active agent is preferably used. Examples of the surface-active agent other than polyvinyl alcohol include lecithin, hydroxymethyl cellulose and hydroxypropyl cellulose.

Examples of the good solvent include: halogenated alkanes, which are organic solvents having a low boiling point; acetone; methanol; ethanol; ethyl acetate; diethyl ether; cyclohexane; benzene; and toluene. For example, acetone or a mixed solution of acetone and ethanol, which only slightly affects the environment and humans, is preferably used.

The concentration of the polyvinyl alcohol aqueous solution, the mixing ratio of acetone and ethanol and conditions for crystal precipitation are not particularly limited; they are determined as appropriate according to the type of target bioactive substance, the diameter of a spherical granulated particle (of the order of a nanometer in the present invention) and the like. However, as the concentration of the polyvinyl alcohol aqueous solution is increased, polyvinyl alcohol is more satisfactorily adhered to the surface of the nanoparticles and is more redispersed into water after drying whereas, when the concentration of the polyvinyl alcohol aqueous solution is equal to or more than a predetermined concentration, the viscosity of the poor solvent is increased, and this affects the diffusibility.

Hence, although depending on the degree of polymerization of and the degree of saponification of polyvinyl alcohol, when the organic solvent is removed after the generation of the nanoparticles, and then powderization is temporarily performed such as by freeze-drying, the concentration of the polyvinyl alcohol aqueous solution is preferably 0.1 weight percent or more but 10 weight percent or less, and more preferably about 2 weight percent. When the organic solvent is distilled away from the suspension after the generation of the nanoparticles, and the remainder is directly used in the nanoparticle adherence step, the concentration of the polyvinyl alcohol aqueous solution is preferably 0.5 weight percent or less, and particularly preferably about 0.1 weight percent.

Preferably, the biocompatible polymer used in the present invention is less irritating and toxic, and biocompatible, and is so biodegradable as to be decomposed and metabolized after being administrated. The biocompatible polymer preferably forms particles that continuously and gradually release the entrapped bioactive substance. In particular, as this type of material, the PLGA can be preferably used.

The molecular weight of the PLGA preferably ranges from 5000 to 200000, and more preferably ranges from 15000 to 25000. The composition ratio of lactic acid to glycolic acid ranges from 1:99 to 99:1, and is preferably 1:0.333. Since the PLGA having a 25 to 65 weight percent content of lactic acid and glycolic acid is amorphous and is soluble in an organic solvent such as acetone, it is preferably used.

Other examples of the biodegradable and biocompatible polymer include polyglycolic acid (PGA), polylactic acid (PLA) and polyaspartic acid. Their copolymers, namely, an aspartic acid-lactic acid copolymer (PAL) and an aspartic acid-lactic acid-glycolic acid copolymer (PALG), may be used, and may have a charge group such as amino acid or a group that can serve as a functional group.

When the bioactive substance entrapped is hydrophilic (water-soluble), the PLGA whose surface is modified by polyethylene glycol (PEG) is preferably used because the affinity between the hydrophilic bioactive substance and the PLGA is enhanced and this facilitates the entrapping.

Still other examples of the biocompatible polymer include: polyalkylene such as polyethylene and polypropylene; polyvinyl compounds such as polyvinyl alcohol, polyvinyl ether and polyvinyl ester; polyamide; polycarbonate; polyethylene glycol; polyethylene oxide; polyethylene terephthalate; polymers of acrylic acid and methacrylic acid; cellulose and other polysaccharides; peptides and proteins; and their copolymers and mixtures.

Thereafter, the suspension of the nanoparticles obtained is used in the subsequent nanoparticle adherence step, without being processed or after undergoing the following process: the organic solvent, that is, the good solvent is distilled away under reduced pressure (solvent distillation step) as required, and then the nanoparticles are temporarily powdered such as by freeze-drying as required and are thereafter dispersed in water again. The use of the suspension of the nanoparticles in the subsequent step without it being processed is preferable because it can eliminate the need for the freeze-drying to simplify the manufacturing process, and reduce the amount of polyvinyl alcohol added to the poor solvent.

When the nanoparticles are temporarily powdered, it is preferable to combine the nanoparticles with a binding agent (for example, trehalose) to form redispersible aggregate particles, that is, combined particles because the aggregate particles, where the nanoparticles are gathered, are easy to handle before being used, and are returned to the redispersible nanoparticles as a result of the binding agent being dissolved through contact with water at the time of use.

The biocompatible nanoparticles used in the present invention are not particularly limited as long as they have an average diameter of less than 1000 nm; in order to introduce the bioactive substance into a stenosis where the catheter is indwelt, it is necessary to incorporate the nanoparticles into cells. In order for the nanoparticles to more effectively penetrate target cells, the average diameter of the nanoparticles is preferably 500 nm or less.

Examples of the bioactive substance entrapped into the biocompatible nanoparticles include: aspirin; dipyridamole; heparins; antithrombin preparations; antiplatelet drugs such as fish oil; low-molecular-weight heparins; smooth muscle growth inhibitors such as angiotensin-converting enzyme inhibitors; vincristine sulfate; vinblastine sulfate; vindesine sulfate; irinotecan hydrochloride; paclitaxel; docetaxel hydrate; methotrexate; anticancer agents such as cyclophosphamide; antibiotics such as mitomycin C; immunosuppressive agents such as sirolimus and tacrolimus hydrates; anti-inflammatory drugs such as steroids; lipid improving drugs such as atorvastatin calcium and lovastatin; nucleic acid compounds such as plasmid DNAs, genes, siRNAs, decoy nucleic acid medicines (decoy), polynucleotides, oligonucleotides, antisense oligonucleotides, ribozymes, aptamers, interleukins and intercellular messengers (cytokines); and receptor tyrosine kinase inhibitors such as Gleevec and PTK787. However, the bioactive substance is not limited to these substances. Any one of the bioactive substances mentioned above may only be entrapped; when a plurality of bioactive substances having components of different effects and action mechanisms are entrapped, their efficacy can be expected to be increased by the synergistic effects of the components.

In particular, when the nanoparticles entrapping a nucleic acid compound are adhered, since the nucleic acid compound can be safely and effectively introduced into a stenosis using a catheter, it is possible to provide an effective treatment in which the stenosis is treated based on nucleic acids and the likelihood of recurrence is low. As the nucleic acid compound, plasmid DNAs, genes, decoys, siRNAs, oligonucleotides, antisense oligonucleotides, ribozymes and aptamers are particularly preferable. The amount of bioactive substance entrapped into the nanoparticles can be adjusted by changing the amount of bioactive substance added at the time of formation of the nanoparticles, the type of cationic polymer and the amount of cationic polymer added and the type of biocompatible polymer forming the nanoparticles.

By entrapping into the nanoparticles an NFκB decoy oligonucleotide (hereinafter, referred to as an "NFκB decoy"), among nucleic acid compounds, that inhibits the generation of a cytokine or the like which binds to an NFκB to cause an inflammation, it is possible to reduce an acute phase inflammatory response when PTA is performed, and thereby effectively prevent restenosis.

In this specification, the term "decoy" refers to a so-called "decoy molecule" having a structure similar to a binding domain on the genome to which a transcription factor itself needs to bind. Under the presence of the decoy, part of the transcription factor does not bind to the target binding domain on the genome but binds to the decoy functioning as a "decoy" for the binding domain. Hence, the number of molecules of the transcription factor binding to the target binding domain is decreased, and this reduces the activity of the transcription factor.

As the decoy, an oligonucleotide in which nucleotides are linked to both ends of a binding sequence is commonly used. The nucleotide portion on each end of the binding sequence is also called an additional sequence, and is composed of one or more bases, and is preferably composed of 1 to 20 nucleotides, more preferably 1 to 10 nucleotides and further preferably 1 to 7 nucleotides. The total chain length of the decoy is not limited, and is normally 15 to 35 nucleotides, preferably 16 to 30 nucleotides and more preferably 17 to 25 nucleotides.

The NFκB decoy is a double-stranded oligonucleotide including one or more binding sequences for an NFκB; preferably, the sequences of these two strands are completely complementary. Specifically, as a typical example of the NFκB decoy, a double-stranded oligonucleotide can be taken that is composed of: a sense-strand oligonucleotide having a configuration of 5'-5' terminal additional sequence-binding sequence-3' terminal additional sequence-3'; and its complementary antisense strand.

Even when one or more (generally one or two) noncomplementary base pairs are contained in an oligonucleotide, such an oligonucleotide is included in NFκB decoys described in this specification as long as it can bind to the NFκB. As another example of the NFκB decoy, a double-stranded oligonucleotide can also be taken that has a plurality of transcription factor binding sites in which a plurality of binding sequences are linked between the 5' terminal additional sequence and the 3' terminal additional sequence, either directly tandemly or with one to few nucleotides interposed.

Moreover, even a single-stranded nucleotide that has a blinding sequence and its complementary sequence within the molecule both of which constitute a double-strand within the molecule and that is a so-called ribbon-shaped decoy or staple-shaped decoy is also included in the NFκB decoys described in this specification as long as it can bind to the NFκB.

It is possible to newly and molecularly design, as a specific example of the NFκB decoy, an NFκB decoy based on the description of, for example, "Current Drug Targets. 2003 November; 4(8): 602-8. It is also possible to use a known NFκB decoy such as sequence number 1 disclosed in "Circ Res. 2001 Nov. 9; 89(10): 899-906.", sequence number 2 disclosed in "FASEB J. 2000 April; 14(5): 815-22." or sequence number 3 disclosed in "Journal Invest Dermatol. 2006 August; 126(8): 1792-803."

As a method of manufacturing the NFκB decoy used in the present invention, a nucleic acid synthesis method, which is commonly used in genetic engineering, can be used. For example, the NFκB decoy may be directly synthesized with a DNA synthesizer, or an oligonucleotide or part thereof may be synthesized and then amplified by a PCR method, a cloning vector method or the like. Furthermore, the oligonucleotide thus obtained is cleaved such as by a restriction enzyme, joined such as by a DNA ligase or processed otherwise; in this way, the NFκB decoy may be manufactured.

The NFκB decoy used in the present invention may include one or more modified bonds or nucleic acids. Examples of the modified bond include: phosphorothioates; methyl phosphates; phosphorodithioates; phosphoroamidates; borano phosphates; methoxyethyl phosphates; and morpholino phosphoroamidates. Examples of the modified nucleic acid include: peptide nucleic acids (PNAs); locked nucleic acids (LNAs); and nucleic acids having bases modified by dinitrophenylation (DNP), O-methylation and the like. Among the bonds mentioned above, phosphorothioates are more preferable.

Although the dinitrophenylation (DNP), the O-methylation and the like are generally used to modify a ribonucleoside (RNA), in the present invention, as with the RNA, it is possible to synthesize an oligonucleotide and modify a base, that is, a deoxyribonucleoside (DNA) to be modified within the oligonucleotide.

It is possible to determine, by a binding activity test, whether or not an oligonucleotide that is either a decoy or a decoy candidate binds to a transcription factor. For the NFκB decoy, the binding activity test for the NFκB can easily be performed with, for example, "TransAM NFκB p65 Transcription Factor Assay Kit (product name, made by Active Motif, Inc.) based on material attached to the kit or through the modification of its protocol to substantially the same extent as that daily performed by a person skilled in the art.

(Negative-Charge-Modification Step)

Figure 3:
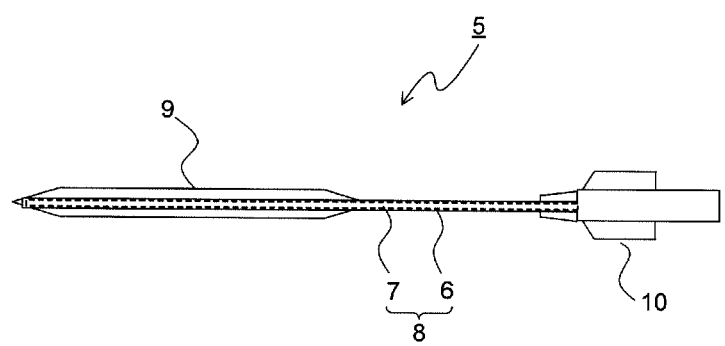
FIG. 3 A side view showing an example of a balloon catheter main body used in the drug-eluting catheter of the present invention.

A method of negative-charge-modifying the balloon portion of the catheter main body will now be described. FIG. 3 is a side view showing an example of the catheter main body used in the present invention. The catheter main body 5 is formed with: a flexible catheter shaft 8 composed of an outer tube 6 and an inner tube 7 inserted into the outer tube 6; and the balloon portion (expandable portion) 9 provided on one end of the catheter shaft 8. On the other end of the catheter shaft 8, a catheter hub 10 is provided that has a hemostasis valve for preventing blood from flowing out.

The catheter main body 5 is introduced into a blood vessel through a sheath with which to prick the hand or foot of a patient, and is further inserted into a stenosis within the blood vessel by a guide wire (not shown) inserted through the catheter hub 10 into the inner tube 7. Then, air or expanded liquid is fed in through a gap between the outer tube 6 and the inner tube 7 under a predetermined pressure, and thus the balloon portion 9 is inflated such that the size of the stenosis approaches the normal diameter of the blood vessel.

Examples of materials used in the catheter shaft 8, the balloon portion 9 and the catheter hub 10 include: thermoplastic resins such as polyethylene, polypropylene, ethylene-propylene copolymers, ethylene-vinyl acetate copolymers, cross-linked ethylene-propylene copolymers, cross-linked ethylene-vinyl acetate copolymers and polyvinyl chlorides; polyamides; polyurethanes; polyesters; and polyarylene sulfides. Among them, polyamides are preferably used, which are easily molded, are appropriately elastic and are unlikely to break. By injecting a contrast agent into the balloon portion 9 formed of an X-ray transparent material and thereby inflating it, it is possible to check, with a monitor, the position of the catheter main body 5 within the blood vessel and the state of the expanded balloon portion 9.

As previously described in the discussion of the nanoparticle formation step, since the surface of the nanoparticles used in the present invention is positively charged, it is possible to heavily and uniformaly coat the balloon portion 9 with the nanoparticles by previously negative-charge-modifying the balloon portion 9 and electrically adhering the nanoparticles. As a method of negative-charge-modifying the balloon portion 9, a method of forming a negatively charged resin layer on the surface of the balloon portion 9 with a negatively charged resin such as a polycarboxylic acid or a polycarboxylic acid derivative is preferably used.

Examples of the polycarboxylic acid used in the present invention include: polymers of acrylic acid, methacrylic acid, maleic acid, fumaric acid, aspartic acid and glutamic acid; carboxymethyl derivatives of starch, cellulose and polyvinyl alcohol; alginic acid; and pectin. One of them or a mixture of two or more of them is used.

Examples of the polycarboxylic acid derivative include acid anhydrides and ester derivatives of the polycarboxylic acids mentioned above. With an acid anhydride derivative or ester derivative of a polymer of acrylic acid, methacrylic acid or maleic acid among them, it is possible to perform the negative-charge-modification less irritating and toxic to humans. Examples of the desirable polycarboxylic acid derivative include: maleic anhydride-methyl vinyl ether copolymers; maleic anhydride-styrene copolymers; and maleic anhydride copolymers such as maleic anhydride-ethylene copolymers, which are easily available and handled. In particular, maleic anhydride-methyl vinyl ether copolymers are preferably used.

Examples of a method of performing coating with the negatively charged resin layer include: a method of dipping the balloon portion 9 of the catheter main body 5 into a solution of the negatively charged resin; a method of spraying minute droplets of the negatively charged resin solution on the surface of the balloon portion 9 using an ultrasonic mist method, a spray method, an airbrush method or the like; and a method of applying the negatively charged resin solution to the surface of the balloon portion 9 using a wiping method.

(Nanoparticle Adherence Step)

A method of adhering the biocompatible nanoparticles entrapping the bioactive substance to the negative-chargemodified balloon portion and thereby forming the nanoparticle layer will now be described. Examples of the method of adhering the nanoparticles include: a method of dipping into the suspension of the nanoparticles the balloon portion 9 of the catheter main body 5 where the negatively charged resin layer is formed; and a method of adhering droplets containing the nanoparticles to the balloon portion 9 using the ultrasonic mist method, the spray method, the airbrush method or the like.

Figure 4:
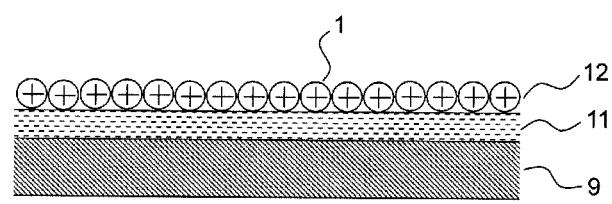
FIG. 4 An enlarged cross-sectional view showing a state where a nanoparticle layer is formed on a balloon portion of the catheter main body.

FIG. 4 is an enlarged cross-sectional view showing a state where the nanoparticles are adhered to the balloon portion of the catheter main body. The surface of the balloon portion 9 is negative-charge-modified by the negatively charged resin layer 11, the surface of the negatively charged resin layer 11 is completely coated by the positively charged nanoparticles 1 and thus the nanoparticle layer 12 is formed.

Hence, it is possible to prevent the nanoparticle layer 12 from being detached from the balloon portion in the subsequent production process and at the time of insertion into a living body and of expansion of the catheter. The adherence of the nanoparticle layer 12 to the negatively charged resin layer 11 is increased probably because of van der Waals force and the like acting between the nanoparticles 1.

As the shape of the catheter main body, various types of conventionally known shapes can be used in addition to that shown in FIG. 3. Preferably, the size of the catheter main body is selected as appropriate according to the area where the catheter main body is applied. For example, when the catheter main body is used in a coronary artery of a heart, it is preferable that, in general, the outside diameter of the catheter main body approximately range from 1.0 to 3.0 mm and its length approximately range from 5.0 to 50 mm before it is expanded.

When the bioactive substance entrapped into the nanoparticles is anionic, the further addition of the bioactive substance to the suspension of the nanoparticles 1 at the time of formation of the nanoparticle layer 12 on the surface of the negatively charged resin layer 11 allows the nanoparticle to be attracted and adhered to the negatively charged resin layer 11 with the bioactive substance electrostatically carried by positive charges on the surface of the nanoparticles. Thus, it is possible to more efficiently adhere an anionic bioactive substance, such as a nucleic acid or a gene, with which it is extremely difficult to coat the balloon portion 9 at a high concentration.

By repeating a plurality of times the above-described methods such as the dipping method, the ultrasonic mist method, the spray method and the airbrush method, it is also possible to deposit another nanoparticle layer on the nanoparticle layer. Since, in this way, a new nanoparticle layer is deposited along the uniform nanoparticle layer 12 formed on the surface of the balloon portion 9 through the negatively charged resin layer 11, it is possible to uniformly and efficiently form a nanoparticle layer having a desired thickness even if the number of nanoparticles adhered per unit time is increased.

A plurality of types of nanoparticles entrapping different types of bioactive substances are produced, and each type of nanoparticle may be adhered in a layer or in a mosaic pattern. Here, nanoparticles entrapping a bioactive substance desired to be eluted in a short period of time after the catheter is indwelt are adhered to an external layer, and nanoparticles entrapping a bioactive substance desired to be eluted after the external layer collapses are adhered to an internal layer, and thus it is possible to control, in a planned manner, periods during which two or more types of bioactive substances are eluted from the balloon portion. Two or more types of bioactive substances are entrapped into nanoparticles of different types of and different molecular weights of biocompatible polymers, and periods during which they are eluted may be controlled.

When the nanoparticle layer 12 formed on the surface of the balloon portion 9 is not further processed, it is likely that the bioactive substance is eluted in a relatively short period of time after the carter is indwelt in a living body and this makes it difficult to control the maintenance of the efficacy. When the nanoparticle layer 12 is completely dried, it is also likely that the nanoparticles more strongly aggregate, the nanoparticle layer 12 becomes an insoluble film, the nanoparticles 1 are not eluted from the surface of the balloon portion 9 and this prevents them from being incorporated into cells. To overcome this problem, it is possible to form the nanoparticle layer 12 in the nanoparticle adherence step, then impregnate the nanoparticle layer with a biodegradable polymer solution as required before the nanoparticle layer is completely dried (impregnation step) and thereafter dry the biodegradable polymer to solidify the nanoparticle layer 12 (drying step).

Figure 5:
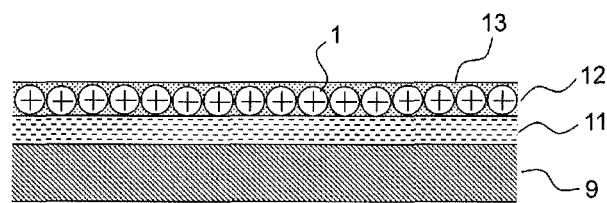
FIG. 5 An enlarged cross-sectional view showing a state where a biodegradable polymer layer is formed on the balloon portion having the nanoparticle layer formed.

In FIG. 5, a state is shown where, in the impregnation step and the drying step, the biodegradable polymer layer is formed on the balloon portion (see FIG. 4) having the nanoparticle layer formed thereon. When the nanoparticle layer 12 is impregnated with the biodegradable polymer solution before the nanoparticle layer 12 formed on the surface of the negatively charged resin layer 11 is completely dried, the biodegradable polymer solution penetrate the gaps between the nanoparticles 1 forming the nanoparticle layer 12. Then, a solvent used to dissolve the biodegradable polymer and the water remaining in the nanoparticle layer 12 are dried, and thus a biodegradable polymer layer 13 is formed. In this way, the individual nanoparticles 1 are retained by the biodegradable polymer without aggregating, and, after the catheter main body is indwelt in the living body, the nanoparticles 1 are gradually eluted by the decomposition of the biodegradable polymer layer 13, and are incorporated into, for example, vascular endothelial cells.

Examples of the biodegradable polymer include: microbe-produced polymers such as polyhydroxybutyrate and polyhydroxyvalerate; and natural polymers such as collagens, cellulose acetates, bacterial celluloses, high-amylose cornstarches, starches and chitosans. Among them, collagens and the like, which decompose more rapidly in vivo than biocompatible polymers, such as PLGAs, used for forming the nanoparticles, are preferably used. The type, the molecular weight and the like of these biodegradable polymers are selected as appropriate, and thus it is possible to control the rate at which the nanoparticles adhered to the surface of the balloon portion are diluted. The biodegradable polymer layer can be formed with a biocompatible polymer, such as a PGA, a PLA, a PLGA or a PAL, that is used to form the nanoparticles; in that case, a biocompatible polymer of low molecular weight is preferably used such that its decomposition rate is faster than the rate at which the nanoparticles are decomposed.

Moreover, the further addition of the bioactive substance to the biodegradable polymer solution with which the nanoparticle layer is impregnated allows the bioactive substance entrapped into the biodegradable polymer outside the nanoparticles to act rapidly and the bioactive substance entrapped into the nanoparticles to act slowly and continuously. The type of bioactive substance and the amount of bioactive substance entrapped can be set as appropriate according to the action mechanism of the bioactive substance, how rapidly and how continuously the bioactive substance is required to act and the like.

Specifically, a bioactive substance required to continuously act over a long period of time after the administration is preferably entrapped into the nanoparticles; a bioactive substance required to effectively act immediately after the administration is preferably entrapped into the biodegradable polymer layer outside the nanoparticles. As the bioactive substance entrapped into the biodegradable polymer layer, the various bioactive substances shown as examples of the bioactive substance entrapped into the nanoparticles can be used.

Figure 6A:
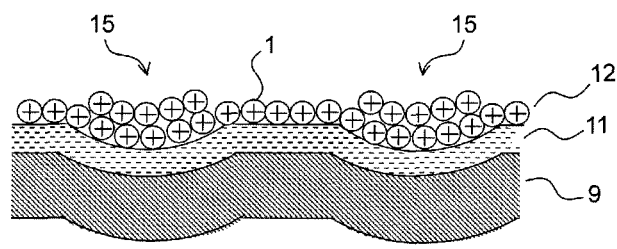
FIG. 6A An enlarged cross-sectional view showing a state where a negatively charged resin layer and the nanoparticle layer are placed on the balloon portion having recesses formed.

When minute recesses are formed in the surface of the balloon portion 9 (see FIG. 3), the depth of the recesses is gradually reduced as the balloon portion 9 is expanded. When the balloon portion 9 is in its completely expanded state, the recesses are not present, and the surface of the balloon portion 9 is flat. Hence, when, as shown in FIG. 6A, the negatively charged resin layer 11 and the nanoparticle layer 12 are placed on the surface of the balloon portion 9 where recesses 15 are formed, a larger number of nanoparticles 1 are carried into the recesses 15 than on the other portions. The negatively charged resin layer 11 and the nanoparticle layer 12 are formed in the same manner as they are formed on the balloon portion 9 having no recesses 15.

Figure 6B:
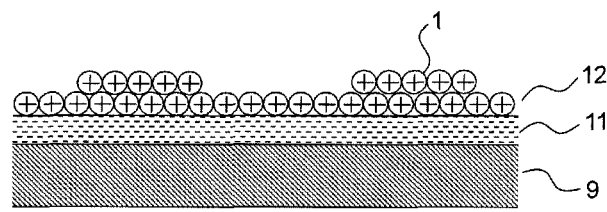
FIG. 6B An enlarged cross-sectional view showing a state where the balloon portion is expanded.

When the catheter is inserted into a stenosis of a blood vessel and then the balloon portion 9 is expanded, the depth of the recesses 15 is gradually reduced. When the balloon portion 9 is in its completely expanded state under a pressure of 5 to 30 atms, the recesses 15 are not present as shown in FIG. 6B, and the nanoparticles 1 are pushed out of the recesses 15 and are pressed against the vascular wall of the stenosis. Thus, it is possible to effectively adhere a large number of nanoparticles 1 to the vascular wall.

The recess 15 is preferably circular or elliptical in shape because the expansion of the balloon portion 9 easily deforms or eliminates the recess of such a shape. When the recess is circular, the diameter of the recess preferably ranges from 0.5 to 5 mm; when the recess is elliptical, the minor axis preferably ranges 0.5 to 5 mm and the value of the major axis/the minor axis preferably ranges from 1 to 5. Preferably, the depth of the recess 15 ranges from 0.1 to 1 mm, the distance between the recesses ranges from 1 to 5 mm and about 10 to 100 recesses are provided in the balloon portion 9.

Since, in the drug-eluting catheter obtained as described above, the surface of the nanoparticles adhered to the balloon portion is positively charged, the adherence of the nanoparticles eluted from the surface of the balloon portion to cells is increased. Thus, the nanoparticles can be introduced into the cells of the stenosis where the catheter is indwelt more effectively than in the conventional drug-eluting catheter.

The present invention is not limited to the embodiments described above; many modifications are possible. Embodiments obtained by combining as appropriate technical means disclosed in different embodiments are also covered by the technical scope of the present invention. The above embodiments deal with only the balloon catheter that is inserted into a blood vessel to keep it open; needless to say, the present invention can likewise be applied to a dilatation catheter that is inserted into a lumen in vivo other than a blood vessel. The preparation of PLGA nanoparticles which entrap an NFκB decoy and whose surface is positive-charge-modified, the production of a drug-eluting balloon catheter coated with the PLGA nanoparticles and how the NFκB decoy is diluted from the surface of a balloon will be specifically described below along with examples.

[Preparation for the PLGA Nanoparticles Containing the NFκB Decoy]

EXAMPLE 1

50 mg of the NFκB decoy indicated by sequence number 1 was dissolved in 6 ml of purified water. 1 g of lactic acid/glycolic acid copolymer (PLGA: PLGA7520 (product name) made by Wako Pure Chemical Industries, Ltd. with a molecular weight of 20000 and a lactic acid/glycolic acid molar ratio of 75 to 25), which was a biocompatible polymer, was dissolved in 43 ml of acetone, which was a good solvent for the acid copolymer, and thus a polymer solution was obtained. Then, the aqueous solution of the NFκB decoy was added to and mixed with the polymer solution, and thus a mixed solution was obtained. 5 g of a 2 weight percent cationic chitosan (Moiss Coat PX (product name) made by Katakura Chikkarin Co., Ltd.) aqueous solution was mixed with 25 ml of a 2 weight percent polyvinyl alcohol (PVA: Poval 403 (product name) made by Kuraray Co., Ltd. with a degree of polymerization of about 300 and a degree of saponification of about 80 mole percent) aqueous solution, and thus a poor solvent was obtained. The mixed solution was dropped into this poor solvent at a constant rate of 4 ml/minute at a temperature of 40° C. while stirred at 400 rpm, and then the good solvent was diffused, with the result that a suspension of the PLGA nanoparticles was obtained.

Then, the acetone was distilled away under a reduced pressure, and the excess polyvinyl alcohol was thereafter removed by centrifugation (20000 rpm, 20 minutes), and the resulting solution was freeze-dried at a temperature of minus 45° C. into powder, with the result that an NFκB decoy-containing PLGA nanoparticle powder having satisfactory water redispersibility was obtained.

EXAMPLE 2

50 mg of the NFκB decoy indicated by sequence number 1 was dissolved in 6 ml of purified water. 1 g of lactic acid/glycolic acid copolymer (PLGA: PLGA7520 (product name) made by Wako Pure Chemical Industries, Ltd.), which was a biocompatible polymer, was dissolved in 43 ml of acetone, which was a good solvent for the acid copolymer, and thus a polymer solution was obtained. Then, the aqueous solution of the NFκB decoy was added to and mixed with the polymer solution, and thus a mixed solution was obtained. 5 g of a 2 weight percent cationic chitosan (Moiss Coat PX (product name) made by Katakura Chikkarin Co., Ltd.) aqueous solution was mixed with 25 ml of a 2 weight percent polyvinyl alcohol (PVA: Poval 403 (product name) made by Kuraray Co., Ltd.) aqueous solution, and thus a poor solvent was obtained. The mixed solution was dropped into this poor solvent at a constant rate of 4 ml/minute at a temperature of 40° C. while stirred at 400 rpm, and then the good solvent was diffused, with the result that a suspension of the PLGA nanoparticles was obtained.

Then, the acetone was distilled away under a reduced pressure, and thereafter 20 mg of the NFκB decoy was further added to the nanoparticle suspension obtained, and the resulting solution was freeze-dried at a temperature of minus 45° C. into powder, with the result that an NFκB decoy containing/surface-carrying PLGA nanoparticle powder was obtained which had the NFκB decoy carried on the surface of the nanoparticles, which entrapped the NFκB decoy into the nanoparticles and which had satisfactory water redispersibility.

The average particle diameter of the PLGA nanoparticles obtained in examples 1 and 2 when they were redispersed into water was measured by dynamic light scattering (measuring device: Microtrac UPA (product name) made by Honeywell Inc.). The zeta potential of the surface of the particles that had been freeze-dried was measured with a zeta potentiometer (Zetasizer Nano-Z (product name) made by Malvern Instruments Ltd.). The content of the NFκB decoy in the particle (weight ratio of the NFκB decoy to the PLGA nanoparticle) was measured with an ultraviolet and visible spectrophotometer (V-530 (product name), made by JASCO Corporation at a measurement wavelength of 260 nm). The measurement results are shown in Table 1. The structure of the nanoparticles obtained in examples 1 and 2 are shown in FIGS. 1 and 2.

TABLE 1

| | Average particle diameter [nm] | Zeta potential [mV] | NFκB decoy content [%] (theoretical value)* |
|---|---|---|---|
| Example 1 | 530 | +0.75 | 4.01(4.35 + 0) |
| Example 2 | 254 | +7.99 | 2.31(0.58 + 1.73) |

The theoretical values of the content (%)=the amount of NFκB decoy prepared for the PLGA nanoparticles×100 are shown separately (for the NFκB decoy contained therein and the NFκB decoy carried thereon).

[Production of a Balloon Catheter Sample for an Elution Test]

EXAMPLE 3

Assembly of the Balloon Catheter Main Body

Hexafluoroisopropanol (HFIP) was applied to part of the polyamide balloon to be adhered and was melted, and the part was adhered to the end of the catheter shaft. A core wire was inserted through the end of the catheter to prevent the entrance of the nanoparticle dispersion solution, and the catheter main body was melted and sealed, with the result that the catheter main body as shown in FIG. 3 was produced.

(The Coating of the Balloon Portion with a Maleic Anhydride Polymer)

The balloon portion of the catheter main body produced was immersed in ethanol (99.5%) for five seconds, and then its surface was wiped with Kimwipes (product name) impregnated with ethanol and was vacuum-dried within a dryer (55° C., 2 hours). Thereafter, in pretreatment for facilitating the coating, the balloon portion was immersed for one hour in a 4 weight percent methyl ethyl ketone solution of hexamethylene-1,6-diisocyanate (HMDI), and was further vacuum-dried within the dryer (55° C., 2 hours).

3 g of a resin composition composed of a 90 weight percent maleic anhydride-methyl vinyl ether copolymer and a 10 weight percent methyl methacrylate-$CH_2$=$C(CH_3)$ $COOCH_2(CF_2)_6CF_3$-styrene-polyurethane-trimethoxyaryl copolymer was dissolved in 100 ml of a mixture solvent (volume ratio 1:1) of tetrahydrofuran and methyl ethyl ketone, with the result that a maleic anhydride polymer coating solution was prepared.

The balloon portion was immersed for five seconds in the maleic anhydride polymer coating solution, and was vacuum-dried within the dryer (55° C., 8 hours). After the drying, in order for a negatively charged carboxyl group to be generated, the balloon portion was immersed in a 0.1 N sodium hydroxide aqueous solution for 20 minutes and was washed with ion exchanged water, with the result that the excess sodium hydroxide was removed. The balloon portion was vacuum-dried within the dryer (55° C., 3 hours), and thus the balloon catheter in which the balloon portion was coated with a maleic anhydride polymer layer (negatively charged resin layer) was produced.

(The Coating of the Balloon Portion with the PLGA Nanoparticles)

The dead spaces (conical portions at both ends of the balloon portion in FIG. 3) of the balloon portion coated with the maleic anhydride polymer layer were previously masked with Parafilm (product name). Then, the 10 weight percent dispersion solution of the NFκB decoy-containing PLGA nanoparticles obtained in examples 1 or 2 was prepared, and the balloon portion was immersed therein for 10 minutes and was then vacuum-dried within the dryer (40° C., 3 hours). The Parafilm (product name) was detached and then the weight of the dried balloon portion was measured, the total number of PLGA nanoparticles adhered was calculated from an increase in weight and the total amount of NFκB decoy adhered was calculated using the content of the NFκB decoy in the particle (see FIG. 1). Until the amount of NFκB decoy adsorbed reached the target value (0.1 mg or more per nanoparticle), the balloon portion was immersed and vacuum-dried a plurality of times (twice for the nanoparticle dispersion solution in example 1 or three times for the nanoparticle dispersion solution in example 2), and thus a balloon catheter sample for an elution test in which the balloon portion was coated with the nanoparticle layer was produced. Five samples of the PLGA nanoparticles in which nanoparticles were coated were produced for each of examples 1 and 2.

[The Elution Test for the NFκB Decoy from the Balloon Catheter]

EXAMPLE 4

Five test tubes (No. 1 to 5) 10 mm in diameter and 90 mm in length were prepated, and 3 ml of saline solution (Pharmacopeia of Japan; pH 6.4) was poured into each of the test tubes. The balloon catheter sample produced in example 3 was sequentially immersed in the saline solution of the test tubes 1 to 5 for each predetermined period shown in table 2.

TABLE 2

| | Test tube No. | | | | |
|---|---|---|---|---|---|
| | 1 | 2 | 3 | 4 | 5 |
| Immersion period (minute) | 0.5 | 1.5 | 8 | 20 | 30 |
| Total immersion period (minute) | 0.5 | 2 | 10 | 30 | 60 |

A syringe having a membrane filter (made of polytetrafluoroethylene; 0.2 μm) connected to its end was prepared, a plunger was removed, the solution in the test tube 1 after the immersion was added to a barrel and the plunger was pushed in to perform filtration. The plunger was removed, 1.2 ml of acetonitrile was added to the barrel, the plunger was inserted in such a position that the solution passed through the filter was about to be discharged from the end of the syringe, the filter was wetted with the acetonitrile, the plunger was removed again and then the syringe was left for 10 minutes. After 10 minutes, the plunger was inserted again to filter the acetonitrile within the syringe, and the acetonitrile was collected in a separate test tube (15 mm in diameter and 150 mm in length).

Then, the plunger was removed, 4.8 ml of a 3.3M sodium chloride/sodium hydroxide aqueous solution (having pH 12 and hereinafter referred to as a "NaCl/NaOH aqueous solution") was added to the barrel, the plunger was inserted in such a position that the solution passed through the filter was about to be discharged from the end of the syringe, the filter was wetted with the NaCl/NaOH aqueous solution, the plunger was removed again and then the syringe was left for 10 minutes. After 10 minutes, the plunger was inserted again to filter the NaCl/NaOH aqueous solution within the syringe, and the NaCl/NaOH aqueous solution was collected in the test tube in which the acetonitrile was collected. Thereafter, the test tube where the acetonitrile and the NaCl/NaOH aqueous solution were collected was shaken with a minishaker for two minutes. At that time, the shaking was performed such that the solution within the test tube was stirred along an inner wall surface of the test tube. The test tubes 2 to 5 were operated in the same manner as described above.

The absorbance of the solution that had been shaken was measured by an ultraviolet-visible spectrophotometer (V-530 (product name) made by JASCO Corporation) at a measurement wavelength of 260 nm at a scanning rate of 100 nm/min, using a quartz cell having an optical path length of 20 mm, while data was acquired at intervals of 1 nm. The amount of NFκB decoy eluted per immersion period was measured by a calibration curve method (where a mixed solution of acetonitrile: the NaCl/NaOH aqueous solution=1:4 was used as a solvent). Moreover, based on the total amount of NFκB decoy adhered, which was calculated in example 3, a dilution rate of the NFκB decoy was measured two minutes after the immersion. The results obtained when the PLGA nanoparticles of example 1 were adhered are shown in FIG. 3; the results obtained when the PLGA nanoparticles of example 2 were adhered are shown in FIG. 4.

TABLE 3

|  |  | Total amount of NFκB decoy discharged [mg] | | | | |
|---|---|---|---|---|---|---|
|  |  | Sample 1 | Sample 2 | Sample 3 | Sample 4 | Sample 5 |
| Total immersion period [minute] | 0.5 | 0.000 | 0.000 | 0.000 | 0.000 | 0.000 |
|  | 2 | 0.000 | 0.000 | 0.000 | 0.000 | 0.000 |
|  | 10 | 0.000 | 0.000 | 0.000 | 0.000 | 0.000 |
|  | 30 | 0.000 | 0.000 | 0.000 | 0.000 | 0.000 |
|  | 60 | 0.000 | 0.000 | 0.000 | 0.000 | 0.000 |
| Total amount of NFκB decoy adhered [mg] |  | 0.148 | 0.156 | 0.172 | 0.192 | 0.152 |
| Dilution rate after two minutes [%] |  | 0 | 0 | 0 | 0 | 0 |

TABLE 4

|  |  | Total amount of NFκB decoy discharged [mg] | | | | |
|---|---|---|---|---|---|---|
|  |  | Sample 1 | Sample 2 | Sample 3 | Sample 4 | Sample 5 |
| Total immersion period [minute] | 0.5 | 0.004 | 0.000 | 0.000 | 0.000 | 0.008 |
|  | 2 | 0.004 | 0.000 | 0.000 | 0.000 | 0.008 |
|  | 10 | 0.004 | 0.000 | 0.000 | 0.016 | 0.021 |
|  | 30 | 0.004 | 0.000 | 0.000 | 0.016 | 0.021 |
|  | 60 | 0.004 | 0.000 | 0.000 | 0.016 | 0.021 |
| Total amount of NFκB decoy adhered [mg] |  | 0.134 | 0.178 | 0.109 | 0.148 | 0.182 |
| Dilution rate after two minutes [%] |  | 3.0 | 0 | 0 | 0 | 4.4 |

As is evident from tables 3 and 4, in the balloon catheter samples to which the nanoparticles of example 1 were adhered, even when all five samples were immersed in the saline solution for 60 minutes, no NFκB decoy was found to be diluted from all the samples. In the balloon catheter samples to which the nanoparticles of example 2 were adhered, although, in two out of the five samples, the NFκB decoy was found to be diluted immediately after the immersion in the saline solution, the dilution rates measured two minutes after the immersion were 3.0% and 4.4%, and the dilution rate of 20% or less was achieved in each of the samples. Although, in one out of the remaining three samples, the NFκB decoy was found to be diluted 10 minutes after the immersion in the saline solution, the amount of NFκB decoy diluted 60 minutes after the immersion was 15% or less in each of the three samples where the dilution was found.

From these results, it has been found that, even when the nanoparticles of any of examples 1 and 2 are adhered, the NFκB decoy is prevented from being disadvantageously released immediately after the catheter is inserted into a living body, and the NFκB decoy can be gradually released for a long period of time from the balloon portion. When the nanoparticles of example 2 were used, the NFκB decoy was found to be slightly eluted; it is estimated that this is because the nanoparticles of example 2 were NFκB decoy containing/surface-carrying nanoparticles and thus the NFκB decoy carried on the surface of the nanoparticles was preferentially eluted.

In order for effects to be produced in these examples in a short period of time, the impregnation step of performing the impregnation with the biodegradable polymer solution was not provided, the nanoparticles were adhered to the balloon portion through the maleic anhydride polymer layer, then the balloon portion was dried without being treated and the catheter sample having the nanoparticle layer formed was used to perform the test. Even when the biodegradable polymer layer is formed on the nanoparticle layer in the impregnation step, it is possible to expect the equivalent or better elution inhibition effects. Here, the NFκB decoy was entrapped (or carried) into the nanoparticles (or on the surface thereof), and the effects of the elution into the living body were examined; it is estimated that, even when various bioactive substances other than the NFκB decoy are entrapped (or carried), similar results are obtained.

[Observation of the Surface of the Balloon Portion with a Fluorescence Microscope]

EXAMPLE 5

In the same manner as in example 2 except that, instead of the NFκB decoy, a fluorescent dye FITC (fluorescein isothiocyanate)-coupled NFκB decoy was added to the suspension of the nanoparticles, NFκB decoy-containing PLGA nanoparticles having the FITC coupled to its surface were produced. A 10 weight percent dispersion solution of the FITC-coupled/NFκB decoy-containing PLGA nanoparticles was prepared, and a balloon catheter sample was produced in the same manner as in example 3.

Figure 7A:
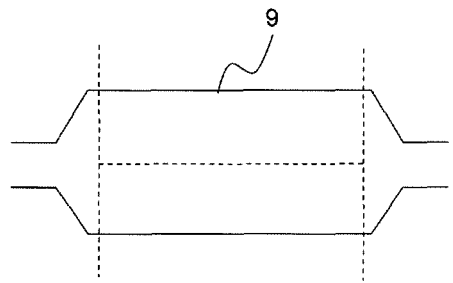
FIG. 7A A diagram showing a method of opening the balloon portion in example 5.
Figure 7B:
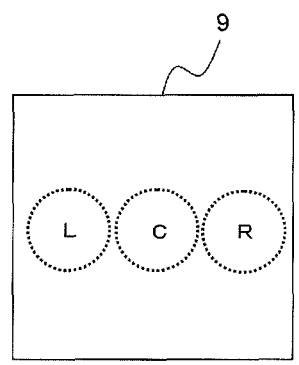
FIG. 7B A diagram showing the observed areas of the balloon portion in example 5.

As shown in FIG. 7A, incisions that were H-shaped as viewed in a horizontal direction were made in the balloon portion of the sample obtained, the balloon portion was opened and sandwiched between glass slides and three areas, namely, L (left), C (center) and R (right), shown in FIG. 7B were observed with the fluorescence microscope as the state before the immersion. The sample after being observed was immersed in 3 ml of the saline solution (Pharmacopeia of Japan; pH 6.4) for one hour, and was then vacuum-dried in the dryer, and the three areas of L, C and R were observed with the fluorescence microscope as the state after the immersion. This sample was further immersed in 2 ml of acetonitrile for 10 minutes, and the three areas of left, center and right were observed with the fluorescence microscope as the state where the nanoparticles were forcibly removed.

The saline solution after the immersion was filtered by the membrane filter (made of polytetrafluoroethylene; 0.2 μm) connected to the syringe, 1.2 ml of acetonitrile was further poured into the barrel and injected into a filter portion, then after 10 minutes, the plunger was completely pushed in and the acetonitrile was collected in the test tube. Furthermore, 4.8 ml of a 3.3M NaCl/NaOH aqueous solution was added to the barrel and injected into the filter portion, then after 10 minutes, the plunger was completely pushed in and the solution was collected in the test tube in which the acetonitrile was collected. Then, the membrane filter was destroyed, the filter portion alone was taken out, and the three areas of L, C and R were observed with the fluorescence microscope.

As observation devices, an inverted research microscope (IX70 made by Olympus Corporation), an inverted epifluorescence observation device (IX-FLA made by Olympus Corporation) and a camera (C-5060-ADU made by Olympus Corporation) were used. The observation was made under conditions that the magnification was 40 times, an excitation cube UMNIBA (470 nm to 490 nm) was used, a laser attenuation filter (94%) was used and the shutter speed was two seconds. The observed results are shown in FIGS. 8 to 11.

Figure 8A:
FIG. 8A A fluorescence micrograph of the balloon portion ("L" shown in FIG. 7B) before immersion in saline solution.
Figure 8B:
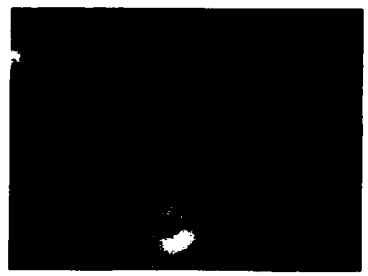
FIG. 8B A fluorescence micrograph of the balloon portion ("C" shown in FIG. 7B) before immersion in saline solution.
Figure 8C:
FIG. 8C A fluorescence micrograph of the balloon portion ("R" shown in FIG. 7B) before immersion in saline solution.
Figure 9A:
FIG. 9A A fluorescence micrograph of the balloon portion ("L" shown in FIG. 7B) that has been immersed in saline solution for 60 minutes.
Figure 9B:
FIG. 9B A fluorescence micrograph of the balloon portion ("C" shown in FIG. 7B) that has been immersed in saline solution for 60 minutes.
Figure 9C:
FIG. 9C A fluorescence micrograph of the balloon portion ("R" shown in FIG. 7B) that has been immersed in saline solution for 60 minutes.
Figure 10A:
FIG. 10A A fluorescence micrograph of the balloon portion ("L" shown in FIG. 7B) that has further been immersed in acetonitrile for 10 minutes after being immersed in saline solution for 60 minutes.
Figure 10B:
FIG. 10B A fluorescence micrograph of the balloon portion ("C" shown in FIG. 7B) that has further been immersed in acetonitrile for 10 minutes after being immersed in saline solution for 60 minutes.
Figure 10C:
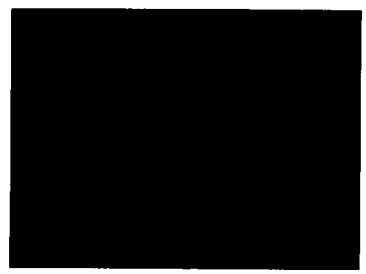
FIG. 10C A fluorescence micrograph of the balloon portion ("R" shown in FIG. 7B) that has further been immersed in acetonitrile for 10 minutes after being immersed in saline solution for 60 minutes.
Figure 11A:
FIG. 11A A fluorescence micrograph of a membrane filter that has filtered the saline solution in which the balloon portion ("L" shown in FIG. 7B) was immersed for 60 minutes.
Figure 11B:
FIG. 11B A fluorescence micrograph of a membrane filter that has filtered the saline solution in which the balloon portion ("C" shown in FIG. 7B) was immersed for 60 minutes.
Figure 11C:
FIG. 11C A fluorescence micrograph of a membrane filter that has filtered the saline solution in which the balloon portion ("R" shown in FIG. 7B) was immersed for 60 minutes.

FIGS. 8 to 10 show fluorescence micrographs of the balloon portion taken before and after the immersion and after the nanoparticles were forcibly destroyed. FIG. 11 is fluorescence micrographs of the membrane filter. In each figure, "A", "B" and "C" indicate the L portion, the C portion and the R portion shown in FIG. 7B, respectively. As is evident from comparison of FIGS. 8 and 10, the strong fluorescence (white portions in the figure) of the FITC was found on the balloon portion before the immersion, and the PLGA nanoparticles were found to be uniformly adhered. As is evident from comparison of FIGS. 8 and 9, even after the nanoparticles were immersed in the saline solution for one hour, they were found to be strongly adhered. On the other hand, as is evident from FIG. 11, in the filter that filtered the saline solution after the immersion of the sample, almost no fluorescence of the FITC was found, and the nanoparticles were found not to be separate from the balloon portion.

EXAMPLE 6

Figure 12A:
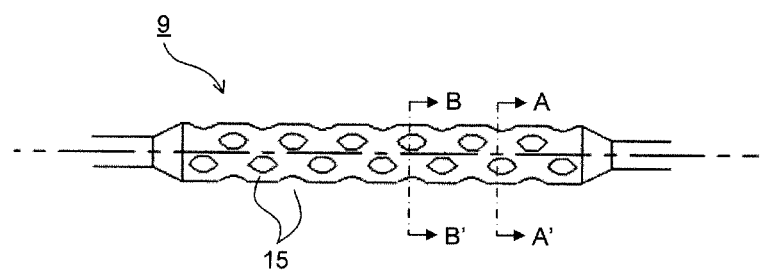
FIG. 12A A side view of the balloon portion where recesses are formed in a surface used in example 6.
Figure 12B:
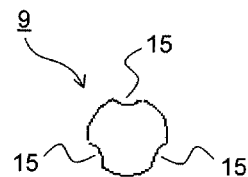
FIG. 12B A cross-sectional view of the balloon portion shown in FIG. 12A taken along line A-A'.
Figure 12C:
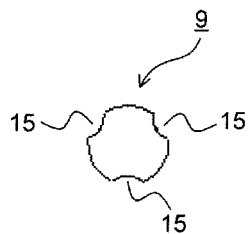
FIG. 12C A cross-sectional view of the balloon portion shown in FIG. 12A taken along line B-B'.

A catheter main body was produced in which, on the surface of the balloon portion 20 mm in effective length and 3 mm in diameter, thirty nine recesses 15 with a diameter of 2 mm and a depth of 0.3 mm were formed so as to be spaced 3 mm apart. The structure of the balloon portion is shown in FIG. 12. FIG. 12A is a side view of the balloon portion; FIG. 12B is a cross-sectional view of the balloon portion taken along line AA'; and FIG. 12C is a cross-sectional view of the balloon portion taken along line BB'. With this catheter main body, a balloon catheter sample was produced in the same manner as in example 5. Compressed air was introduced into the balloon portion of the sample obtained to gradually expand the balloon portion, and changes in the shape of the recesses were observed with the fluorescence microscope. The same observation devices and conditions as in example 5 were used. The observed results are shown in FIG. 13.

Figure 13A:
FIG. 13A A fluorescence micrograph of the balloon portion in example 6 before pressurization.
Figure 13B:
FIG. 13B A fluorescence micrograph of the balloon portion in example 6 after a pressure of 10 atm is applied thereto.
Figure 13C:
FIG. 13C A fluorescence micrograph of the balloon portion in example 6 after a pressure of 20 atm is applied thereto.

Before the introduction of the compressed air into the balloon portion, that is, in the state of equilibrium with the atmospheric pressure (about 1 atm), as shown in FIG. 13A, in the recess, the strong fluorescence of the FITC was observed, and a large number of PLGA nanoparticles were found to be carried. As the pressure of the balloon portion was increased up to 10 atm from the state described above, the depth of the recess and the fluorescence of the FITC were decreased as shown in FIG. 13B. When the pressure was increased up to 20 atm, the balloon portion became free of the recesses as shown in FIG. 13C, and the surface of the balloon portion became flat. Almost no fluorescence of the FITC was observed, and the nanoparticles were found to be pushed out of the recesses.

[Neointimal Formation Inhibition Test Using a PTA Balloon Catheter]

EXAMPLE 7

An abdominal aorta of a male rabbit was scratched, and thus its vascular endothelium was damaged. Immediately afterward, either a PTA balloon catheter (hereinafter, an "NFκB decoy (+) catheter") in which the balloon portion was coated with the NFκB decoy-containing PLGA nanoparticles or a PTA balloon catheter (hereinafter, an "NFκB decoy (−) catheter") in which the balloon portion was not coated was inserted into the damaged area, and the balloon was expanded for one minute (n=6 for each group). The aorta was extirpated four weeks after the treatment of the PTA balloon catheter, an Elastica van Gieson (EVG) stain sample was produced and the area of an intima ($mm^2$), the area of an arterial media ($mm^2$), an average value (mean), a standard deviation (SD) and the area ratio of the intima to the arterial media (I/M) were calculated. The results are shown in Table 5 and FIGS. 17A to 17C. Micrographs showing the cross section of the abdominal aorta of a rabbit whose vascular endothelium was not damaged, of a rabbit of an NFκB decoy (−) catheter group and of a rabbit of an NFκB decoy (+) catheter group are illustrated in FIGS. 14 to 16, respectively.

TABLE 5

|  | NF k B (−) | | NF k B (+) | |
| --- | --- | --- | --- | --- |
|  | Mean | SD | Mean | SD |
| Intima (I) | 1.13 | 0.12 | 0.81 | 0.06 |
| Arterial media (M) | 1.08 | 0.08 | 1.21 | 0.05 |
| I/M ratio | 1.08 | 0.12 | 0.69 | 0.07 |

Figure 14:
FIG. 14 A micrograph (magnification: 40 times) showing a cross section of a normal abdominal aorta of a rabbit whose vascular endothelium was not damaged in example 7.
Figure 15:
FIG. 15 A micrograph (magnification: 40 times) showing a cross section [NFκB decoy (−)] of an abdominal aorta of a rabbit whose vascular endothelium was scratched with a PTA balloon catheter coated with NFκB decoy-free PLGA nanoparticles in example 7.
Figure 16:
FIG. 16 A micrograph (magnification: 40 times) showing a cross section [NFκB decoy (+)] of an abdominal aorta of a rabbit whose vascular endothelium was scratched with a PTA balloon catheter coated with NFκB decoy-containing PLGA nanoparticles in example 7.
Figure 17A:
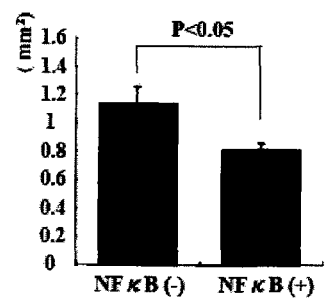
FIG. 17A A graph comparing the area ($mm^2$) of an intima of an abdominal aorta between an NFκB decoy (+) group and an NFκB decoy (−) group in example 7.
Figure 17B:
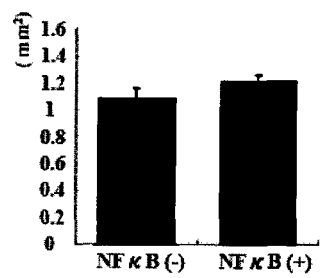
FIG. 17B A graph comparing the area ($mm^2$) of an arterial media of the abdominal aorta between the NFκB decoy (+) group and the NFκB decoy (−) group in example 7.
Figure 17C:
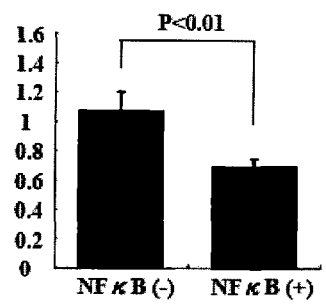
FIG. 17C A graph comparing the area ratio of the intima to the arterial media (I/M) of the abdominal aorta between the NFκB decoy (+) group and the NFκB decoy (−) group in example 7.

As is evident from FIGS. 14 to 16, as compared with the abdominal aorta (FIG. 14) of the rabbit whose vascular endothelium was not damaged, the abdominal aorta (FIG. 15) of the rabbit of the NFκB decoy (−) catheter group was considerably increased in the area of the intima, and the abdominal aorta (FIG. 16) of the rabbit of the NFκB decoy (+) catheter group was only slightly increased in the area of the intima. As is evident from table 5 and FIGS. 17A to 17C, as compared with the NFκB decoy (−) catheter group, in the NFκB decoy (+) catheter group, the area of the intima of the abdominal aorta and the area ratio of the intima to the arterial media were found to be significantly reduced, and the neointimal formation after the intima was damaged was found to be significantly inhibited.

EXAMPLE 8

A carotid artery of a male rabbit was scratched, and thus its vascular endothelium was damaged. Four weeks afterward, either the NFκB decoy (+) catheter or the NFκB decoy (−) catheter was inserted into a stenosis, and the balloon was expanded for one minute. As a control, a control group in which the PTA balloon catheter was not inserted was provided (n=9 for each group). The carotid artery was extirpated four weeks after the treatment of the PTA balloon catheter, an Elastica van Gieson (EVG) stain sample was produced and the area of an intima ($mm^2$), the area of an arterial media ($mm^2$), an average value (mean), a standard deviation (SD) and the area ratio of the intima to the arterial media (I/M) were calculated. The results are shown in Table 6 and FIGS. 18A to 18C.

TABLE 6

|  | Control | | NFkB (−) | | NFkB (+) | |
| --- | --- | --- | --- | --- | --- | --- |
|  | Mean | SD | Mean | SD | Mean | SD |
| Intima (I) | 0.66 | 0.17 | 0.62 | 0.06 | 0.39 | 0.08 |
| Arterial media (M) | 0.52 | 0.07 | 0.60 | 0.03 | 0.61 | 0.05 |
| I/M ratio | 1.49 | 0.51 | 1.05 | 0.11 | 0.63 | 0.12 |

Figure 18A:
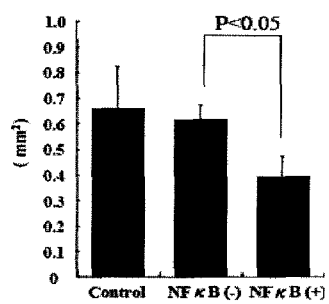
FIG. 18A A graph comparing the area ($mm^2$) of an intima of a carotid artery between a control group, the NFκB decoy (+) group and the NFκB decoy (−) group in example 8.
Figure 18B:
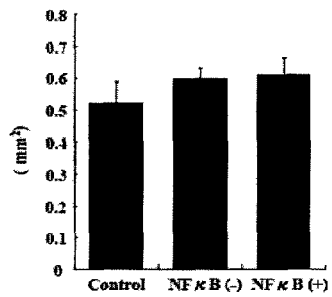
FIG. 18B A graph comparing the area ($mm^2$) of an arterial media of the carotid artery between the control group, the NFκB decoy (+) group and the NFκB decoy (−) group in example 8.
Figure 18C:
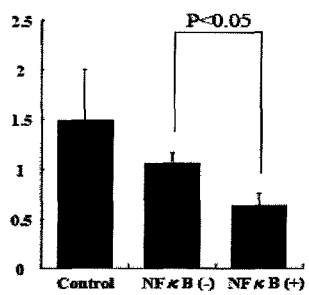
FIG. 18C A graph comparing the area ratio of the intima to the arterial media (I/M) of the carotid artery between the control group, the NFκB decoy (+) group and the NFκB decoy (−) group in example 8.

As is evident from Table 6 and FIGS. 18A to 18C, as compared with the NFκB decoy (−) catheter group and the control group, in the NFκB decoy (+) catheter group, the area of the intima of the carotid artery and the area ratio of the intima to the arterial media were found to be significantly reduced, and the neointimal formation after the intima was damaged was found to be significantly inhibited.

INDUSTRIAL APPLICABILITY

In the drug-eluting catheter of the present invention, the expandable portion negative-charge-modified by a polycarboxylic acid or a polycarboxylic acid derivative is coated with the biocompativle nanoparticles whose surface is positive-charge-modified by a cationic polymer. Thus, the adherence of the nanoparticles diluted in vivo to cells is increased, and the movement of the nanoparticles into the cells is also enhanced. Moreover, since a chitosan is used as the cationic polymer, and any one of a polylactic acid, a polyglycolic acid, a PLGA and a PAL is used as the biocompativle polymer, it is possible to provide the drug-eluting catheter that is highly safe and has excellent stability and sustained-release capability.

By entrapping a nucleic acid compound into the nanoparticles, it is possible to provide the drug-eluting catheter for safely and effectively introducing the nucleic acid compound into an affected area to perform a gene-based treatment. When a plasmid DNA, a gene, a decoy, an siRNA, an oligonucleotide, an antisense oligonucleotide, a ribozyme, an aptamer or the like is used as the nucleic acid compound, it is possible to provide the drug-eluting catheter as a particularly preferred gene therapy tool. By entrapping the NFκB decoy, among nucleic acid compounds, that inhibits the generation of a cytokine or the like which binds to an NFκB to cause an inflammation, it is possible to reduce an acute phase inflammatory response when PTA is performed, and thereby effectively prevent restenosis.

The drug-eluting catheter of the present invention has particularly beneficial effects as an intravascular catheter. As an intravascular catheter, a balloon catheter having a balloon as an expandable portion is preferably used. Here, when circular or elliptical minute recesses are formed in the surface of the balloon, it is possible to provide the drug-eluting catheter that can actively discharge the nanoparticles by the expansion of the balloon.

According to the method of manufacturing the drug-eluting catheter of the present invention, the nanoparticles whose surface is positive-charge-modified are adhered to the negative-charge-modified expandable portion of the catheter. Thus, it is possible to easily and inexpensively manufacture a catheter to which liposoluble and water-soluble bioactive substances having difficulty being adhered to a resin expandable portion are effectively adhered. Moreover, by adhering the nanoparticles a plurality of times, it is possible to uniformly and effectively form the nanoparticle layer having a desired thickness.

It is also possible to provide a method of easily and inexpensively manufacturing the drug-eluting catheter in which the nanoparticle layer is impregnated with the biodegradable polymer and is dried and thus the nanoparticle layer is prevented from becoming an insoluble film, and in which, since the nanoparticles are gradually released from the expandable portion as the biodegradable polymer is decomposed, the catheter is easy to handle and it is possible to control the speed at which the bioactive substance is released.

Nanoparticle layers entrapping different bioactive substances are formed in a layer or a mosaic pattern, a bioactive substance is entrapped into a biodegradable polymer layer with which a nanoparticle layer is impregnated or the type of biodegradable polymer is selected according to the required speed at which the nanoparticles are released. In this way, it is possible to manufacture the drug-eluting catheter that can release the bioactive substance in a planned manner.

What is claimed is:

1. An expandable drug-eluting catheter, comprising:
an expandable portion having a surface;
a first coating on the surface of the expandable portion, the first coating comprising a negatively charged resin; and
a second coating on the surface of the expandable portion, wherein the first coating is between the surface and the second coating, the second coating comprises a polymeric surface active agent and biocompatible nanoparticles, the biocompatible nanoparticles are formed in layers and in contact with each other, and the nanoparticles are positively charged and entrap a bioactive substance.

2. The drug-eluting catheter of claim 1, wherein the negatively charged resin is formed from any compound selected from the group consisting of a polycarboxylic acid, an acid anhydride of a polycarboxylic acid, or an ester of a polycarboxylic acid.

3. The drug-eluting catheter of claim 2, wherein the polycarboxylic acid is one or more selected from the group consisting of polymers of acrylic acid, methacrylic acid, maleic acid, fumaric acid, aspartic acid and glutamic acid; a carboxymethyl substituted starch, cellulose or polyvinyl alcohol; alginic acid; and pectin.

4. The drug-eluting catheter of claim 2, wherein the acid anhydride or ester of polycarboxylic acid is an acid anhydride or ester of a polymer of acrylic acid, methacrylic acid or maleic acid.

5. The drug-eluting catheter of claim 4, wherein the acid anhydride of polycarboxylic acid is a maleic anhydride copolymer.

6. The drug-eluting catheter of claim 5, wherein the maleic anhydride copolymer is one or more selected from the group consisting of a maleic anhydride-methyl vinyl ether copolymer, a maleic anhydride-styrene copolymer and a maleic anhydride-ethylene copolymer.

7. The drug-eluting catheter of claim 1, wherein the biocompatible nanoparticles are positively charged by adhering a cationic polymer to the surface.

8. The drug-eluting catheter of claim 7, wherein the cationic polymer is a chitosan.

9. The drug-eluting catheter of claim 1, wherein the biocompatible nanoparticles are formed of any compound selected from the group consisting of polylactic acid, polyglycolic acid, a lactic acid-glycolic acid copolymer and a lactic acid-aspartic acid copolymer.

10. The drug-eluting catheter of claim 1, wherein the bioactive substance is a nucleic acid compound.

11. The drug-eluting catheter of claim 10, wherein the nucleic acid compound is one or more selected from the group consisting of a plasmid DNA, a gene, a decoy, an siRNA, an oligonucleotide, an antisense oligonucleotide, a ribozyme and an aptamer.

12. The drug-eluting catheter of claim 11, wherein the nucleic acid compound is an NFκB decoy oligonucleotide.

13. The drug-eluting catheter of claim 12, wherein the NFκB decoy oligonucleotide is one selected from SEQ ID NO. 1, SEQ ID NO. 2 and SEQ ID NO. 3.

14. A method of treating a vascular stenosis or a dialysis shunt stenosis, comprising:
inserting the drug-eluting catheter of claim 12 into the stenosis in a blood vessel, and
expanding the expandable portion,
wherein the bioactive substance is subsequently released from the expandable portion, thereby treating the vascular stenosis or dialysis shunt stenosis.

15. The drug-eluting catheter of claim 1, wherein the drug-eluting catheter is a balloon catheter having a balloon as the expandable portion.

16. The drug-eluting catheter of claim 15, wherein a recess is formed in a surface of the balloon.

17. The drug-eluting catheter of claim 16, wherein the recess is circular or elliptical.

18. A method of manufacturing the drug-eluting catheter of claim 1, the method comprising:
a nanoparticle formation step of
adding a mixed solution of at least a solution of bioactive substance and a solution obtained by dissolving a biocompatible polymer in an organic solvent to an aqueous solution obtained by dissolving at least a cationic polymer;
entrapping the bioactive substance into the biocompatible polymer and generating a suspension of a biocompatible nanoparticle whose surface is positive-charge-modified by adding the mixed solution into an aqueous solution comprising a cationic polymer and a surface active agent;
a negative-charge-modification step of negative charge-modifying an expandable portion of a catheter main body by coating the expandable portion surface with a negatively-charged resin;
a nanoparticle adherence step of forming a nanoparticle layer by adhering the biocompatible nanoparticle to the negative-charge-modified expandable portion; and
a drying step of drying the nanoparticle layer.

19. The method of claim 18, wherein the negative-charge-modification step is performed by dipping the expandable portion in a solution of a polycarboxylic acid or a polycarboxylic acid derivative.

20. The method of claim 18, wherein an anionic bioactive substance is further added to the suspension of the biocompatible nanoparticle.

21. The method of claim 18, wherein the nanoparticle adherence step is repeated a plurality of times to further place a nanoparticle layer on the nanoparticle layer formed on the expandable portion.

22. The method of claim 21, wherein the nanoparticle adherence step is repeated a plurality of times to form the nanoparticle layers of biocompatible nanoparticles entrapping different bioactive substances one on top of another or in a mosaic pattern.

23. The method of claim 18, the method further comprising:
   an impregnation step of impregnating the nanoparticle layer with a solution of a biodegradable polymer.

24. The method of claim 23, wherein, in the impregnation step, the bioactive substance is further added to the solution of the biodegradable polymer.

25. The method of claim 23, wherein the biodegradable polymer with which the nanoparticle layer is impregnated in the impregnation step degrades in vivo more rapidly than the biocompatible polymer forming the biocompatible nanoparticle.

* * * * *